United States Patent [19]

Bollinger

[11] 4,273,784

[45] Jun. 16, 1981

[54] ORGANIC COMPOUNDS

[75] Inventor: Pietro Bollinger, Bottmingen, Switzerland

[73] Assignee: Sandoz Ltd., Basel, Switzerland

[21] Appl. No.: 24,558

[22] Filed: Mar. 28, 1979

Related U.S. Application Data

[63] Continuation of Ser. No. 848,814, Nov. 7, 1977, abandoned, which is a continuation of Ser. No. 749,497, Dec. 10, 1976, abandoned, which is a continuation-in-part of Ser. No. 720,315, Sep. 3, 1976, abandoned, and Ser. No. 645,546, Dec. 31, 1975, abandoned, said Ser. No. 720,315 is a continuation-in-part of said Ser. No. 645,546, which is a continuation-in-part of Ser. No. 642,189, Dec. 18, 1975 and Ser. No. 485,310, Jul. 2, 1974, abandoned, said Ser. No. 642,189 is a continuation of said Ser. No. 485,310.

[30] Foreign Application Priority Data

| Jul. 9, 1973 | [CH] | Switzerland | 9959/73 |
| May 4, 1974 | [CH] | Switzerland | 6049/74 |
| Feb. 11, 1975 | [CH] | Switzerland | 1651/75 |
| Sep. 5, 1975 | [CH] | Switzerland | 11593/75 |
| Oct. 1, 1975 | [CH] | Switzerland | 12727/75 |
| Dec. 12, 1975 | [CH] | Switzerland | 16143/75 |
| Dec. 16, 1975 | [CH] | Switzerland | 16281/75 |
| Jan. 7, 1976 | [CH] | Switzerland | 102/76 |
| Jan. 7, 1976 | [CH] | Switzerland | 103/76 |

[51] Int. Cl.$^3$ .............................................. C07C 177/00
[52] U.S. Cl. ................................... 424/305; 560/118; 560/53; 560/60; 560/61; 562/500; 562/463; 562/470; 562/471; 542/426; 424/308; 424/317
[58] Field of Search ............. 560/118; 562/500; 424/305, 317

[56] References Cited

FOREIGN PATENT DOCUMENTS 817383 1/1975 Belgium.

*Primary Examiner*—Robert Gerstl
*Attorney, Agent, or Firm*—Gerald D. Sharkin; Robert S. Honor; Timothy G. Rothwell

[57] ABSTRACT

The present invention concerns prostaglandins having a cyclopropane ring in the 2,3 position.

41 Claims, No Drawings

ORGANIC COMPOUNDS

This is a continuation of application Ser. No. 848,814, filed Nov. 7, 1977, which in turn is a continuation of application Ser. No. 749,497, filed Dec. 10, 1976, which is a continuation-in-part of my co-pending application Ser. No. 720,315 filed Sept. 3, 1976, and of my co-pending application Ser. No. 645,546 filed on Dec. 31, 1975, Ser. No. 720,315, being a continuation-in-part of Ser. No. 645,546, which in turn is a continuation-in-part of my earlier filed then co-pending applications Ser. No. 642,189 filed on Dec. 18, 1975, and Ser. No. 485,310 filed July 2, 1974, Ser. No. 642,189 being in turn a continuation of my co-pending application Ser. No. 485,310, filed July 2, 1974, all now abandoned.

The entire contents of application Ser. No. 485,310 and Ser. No. 645,546 are incorporated herein by reference, including scopes, sub-scopes, processes and claims. Similarly the entire contents of the priority Swiss applications listed in the affirmation including scopes, precise reaction detail species, etc., are also incorporated herein by reference.

The present invention relates to prostaglandins.

The present invention provides racemic or optically active prostaglandins having the ethylene moiety in the 2,3 position replaced by a 1,2-cyclo-propylene moiety.

In particular, the present invention provides a racemic or optically active prostaglandin having a prostaglandin ring, two side chains attached to adjacent positions of said ring, one side chain having a carbonyl group separated from the ring by 6 carbon atoms of said chain, characterized by a methylene group attached across the fifth and sixth carbon atoms of said one side chain reckoned from the prostaglandin ring.

A preferred group of compounds comprise compounds having the structure

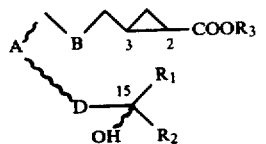

I wherein
A is a group of formula

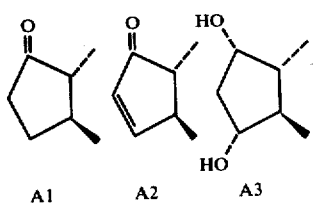

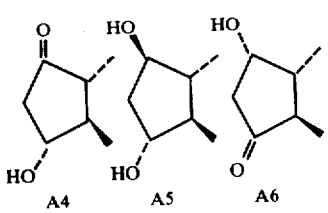

-continued

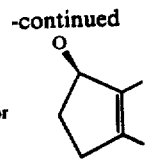

A7

B is $-CH_2-CH_2-$ or (cis)$-CH=CH-$,
D is $-CH_2-CH_2-$ or (trans)$-CH=CH-$,
$R_1$ is
  (i) alkyl of 1 to 10 carbon atoms, or
  (ii) a radical of formula II,

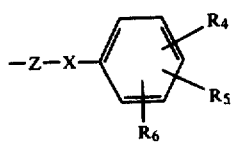

II wherein
Z is alkylene of 1 to 5 carbon atoms,
X is $-CH_2-$ or $-O-$, and
$R_4$, $R_5$, and $R_6$ are, independently, hydrogen, halogen or trifluoromethyl,
$R_2$ is hydrogen or alkyl of 1 to 7 carbon atoms, and
$R_3$ is
  (i) hydrogen,
  (ii) alkyl of 1 to 10 carbon atoms, or
  (iii) alkyl of 1 to 10 carbon atoms, mono- or di-substituted by phenyl or biphenyl,
or when $R_1$ is a radical of formula III,

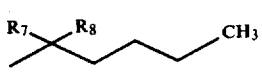

III wherein
$R_7$ and $R_8$ are, independently, hydrogen or alkyl of 1 to 4 carbon atoms,
$R_2$ is hydrogen,
B is (cis)$-CH=CH-$,
D is (trans)$-CH=CH-$, and
A is A1, A2, A3 or A4,
  (iv) cycloalkyl of 3 to 10 carbon atoms, in optically active or racemic form.

In one group of compounds
$R_1$ is a radical of formula III,

III wherein
$R_7$ and $R_8$ are, independently, hydrogen or alkyl of 1 to 4 carbon atoms,
$R_2$ is hydrogen,
A is A1, A2, A3 or A4,
B is (cis)$-CH=CH-$,
D is (trans)$-CH=CH-$, and
$R_3$ is
  (i) hydrogen,
  (ii) alkyl of 1 to 8 carbon atoms,
  (iii) cycloalkyl of 3 to 10 carbon atoms, or
  (iv) aralkyl of 7 to 12 carbon atoms.

In another group of compounds A, B, D, R₁, R₂ and R₃ are as defined above with respect to formula I, with the proviso that when R₁ is a radical of formula III, as defined above, R₂ is hydrogen, B is (cis)—CH=CH—, D is (trans)—CH=CH— and A is a group of formula A1, A2, A3 or A4, then R₃ is hydrogen, alkyl of 1 to 8 carbon atoms, cycloalkyl of 3 to 10 carbon atoms or aralkyl of 7 to 12 carbon atoms.

It is to be appreciated that compounds of formula I and the starting materials mentioned hereinafter may be in racemic form or in individual optical isomer form, which includes optical isomers, wherein A1 to A6 have the absolute configuration depicted as above, or a mirror image thereof of that depicted above.

When the compound is in individual optical isomer form, the 15-OH group preferably is in the same configuration at the 15-carbon atom as the 15-OH group of natural PGE₂, i.e. in the α-configuration.

When the compound is in individual optical isomer form, A is preferably a group of formulae A1 to A6 rather than a mirror image of a group of formulae A1 to A6.

A is preferably A2, A3 or A4, preferably A3 or A4, especially A4.

R₁ is preferably alkyl.

When R₁ is alkyl, this conveniently is a straight chain alkyl, e.g. 1-heptyl or 1-pentyl. Alternatively R₁ is conveniently branched at the α-position, i.e. on the 16-carbon atom of the prostaglandin structure. When the 16-carbon atom is secondary, R₁ may, for example, be 2-hexyl or 5-nonyl, and when the 16-carbon atom is asymmetrically substituted, e.g. as in 2-hexyl, the configuration of the 15- and 16-carbon atoms is preferably identical to that in (15S,16R)-16-methyl-PGE₂. When the 16-carbon atom is tertiary, two of the alkyl substituents are preferably the same and R₁ is, for example, 2-methyl-2-hexyl. Alternatively R₁ is, for example, 1-pentyl, 1-heptyl, 2-methyl-2-hexyl, 2-hexyl or 2-octyl.

When R₁ is a radical of formula II, Z is preferably methylene or isopropylidene. X is —O—.

In another group of compounds X is —CH₂—.

One or especially two radicals of R₄, R₅ and R₆ are preferably hydrogen. A radical of R₄, R₅ and R₆ which is other than hydrogen is preferably in the meta or para position. When one of R₄, R₅ and R₆ is halogen, this is fluorine, chlorine or bromine, preferably fluorine or chlorine. Preferably two radicals of R₄, R₅ and R₆ are hydrogen and one is fluorine in the para-position or trifluoromethyl in the meta-position.

In one group of compounds B is —CH₂—CH₂—. In another group of compounds D is —CH₂—CH₂—.

R₂ is preferably hydrogen. When R₂ is alkyl, this is preferably methyl. When R₂ contains more than two carbon atoms, it preferably has a straight chain of carbon atoms.

R₂ is, for example, methyl, ethyl, n-propyl, isopropyl or iso-butyl.

R₃ is preferably hydrogen or unsubstituted alkyl. When R₃ is substituted alkyl, the alkyl thereof preferably has 1 to 4 carbon atoms, especially 1 carbon atom. When R₃ is alkyl substituted by phenyl, it preferably is disubstituted, the two phenyl groups being especially attached to the same carbon atom, preferably the terminal atom. When R₃ is alkyl substituted by biphenyl, it is preferably mono-substituted. R₃ may be, for example, benzyl, di(phenyl)methyl or biphenylmethyl.

In formula I the substituents of the cyclopropane ring are cis or preferably trans to each other.

The compounds of formula I may be produced by processes well known in the prostaglandin art.

Thus compounds of formula I may be produced by a process comprising splitting off one or more acid-sensitive protecting groups protecting at least one hydroxy group and/or any carboxyl group present in a compound of formula IV,

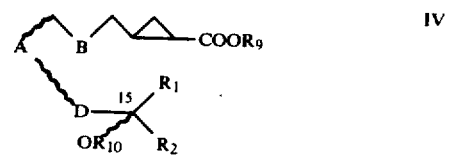

wherein A′ is A as defined above, or a group of formula

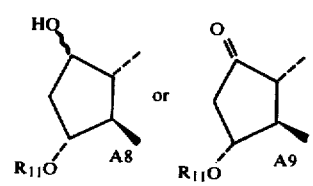

or a mirror image of a group of formula A8 or A9, wherein

R₁₁ is an acid-sensitive protecting group,
B, D, R₁ and R₂ are as defined above,
R₉ is R₃ as defined above or an acid-sensitive protecting group, and
R₁₀ is hydrogen or an acid-sensitive protecting group, or a racemate of a compound of formula IV, with the proviso that there is at least one acid-sensitive protecting group present.

The process may be effected in conventional manner for such deprotecting reactions.

Examples of suitable acid-sensitive protecting groups include tetrahydropyranyl and tert.-butyldimethylsilyl. Suitable acidic media for the reaction include the following mixtures: acetic acid/tetrahydrofuran; hydrochloric acid/acetone; hydrochloric acid/methanol; sulphuric acid/methanol, if desired in the presence of water. Suitable temperatures lie between −10° C. and +50° C., preferably between +10° C. and +30° C.

The starting materials of formula IV and their racemates may be prepared in conventional manner by reacting a compound of formula V,

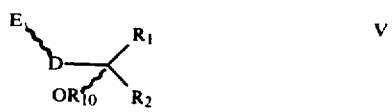

wherein D, R₁, R₂, and R₁₀ are as defined above, and E is a group of formula

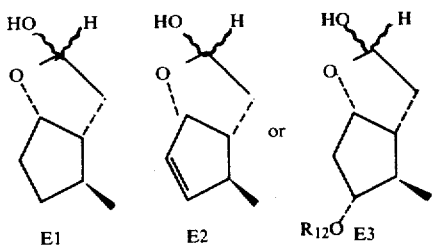

wherein $R_{12}$ is $R_{11}$ as defined above, or hydrogen, or a mirror image of a group of formula E1, E2 or E3, under Wittig conditions with a compound of formula VI,

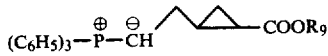

VI wherein $R_9$ is as defined above, to produce a compound of formula VII,

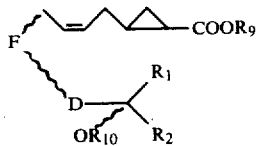

VII wherein F is a group of formula

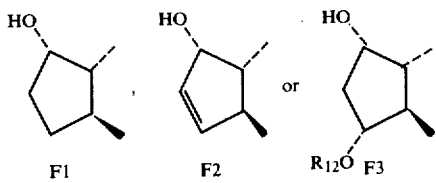

or F is a mirror image of a group of formula F1, F2 or F3, and D, $R_1$, $R_2$, $R_9$, $R_{10}$ and $R_{12}$ are as defined above, then if necessary carrying out one or more of the following reactions to convert a compound of formula VII into a compound of formula IV:

(a) oxidizing the 9-hydroxy group in a group F1 to form a 9-keto group of a compound having a group A1, (b) oxidizing the 9-hydroxy group in a group F2 to form a 9-keto group of a compound having a group A2, and if desired further isomerizing this group A2 into a group A7 by treatment with base, (c) oxidizing the 9-hydroxy group in a group F3 to form a 9-keto group of a compound having a group A4 or A9, and if desired reducing with sodium borohydride (i) the 9-keto group of the group A4 to form a mixture of 9α and 9β alcohols having the group A3 and A5, respectively, or (ii) the 9-keto group of the group A9 to form a mixture of 9α and 9β alcohols having the group A8, and then separating the 9α and 9β alcohols by chromatography, (d) oxidizing the 11-hydroxy group present in a group F3 wherein $R_{12}$ is hydrogen, to form a compound having a group A6 which can be separated from any compound formed having a group A4, (e) catalytically hydrogenating any compound of formula VII to form a corresponding compound wherein the 5,6 double bond is saturated, i.e. B is —CH$_2$—CH$_2$—, and/or (f) protecting any hydroxy and/or carboxyl group present with an acid-sensitive protecting group.

It is appreciated that steps (a) to (f) may alternatively be carried out with compounds of formula VII, wherein F is a mirror image of a group of formula F1, F2 or F3 as starting materials to produce the corresponding compounds of formula IV.

It is also to be appreciated that when racemates of the compounds of formula V are used, racemates of the compounds of formula IV are obtained.

Such reactions and separation procedures are well-known in the prostaglandin art. Generally these reactions are effected under mild conditions. For example, catalytic hydrogenation may be effected at e.g. −40° C. to −10° C. in the presence of palladium in order to selectively hydrogenate a 5,6-double bond in a compound of formula VII, wherein D is trans —CH=CH—.

It is also to be appreciated that the last step in the production of any given prostaglandin may not need to be the splitting off of a protecting group. Instead the above procedures (a) to (e) may be applied, singly or in combination for the interconversion of one prostaglandin of formula I into another prostaglandin of formula I.

Moreover the above-mentioned Wittig reaction may be effected with starting materials of formula V, wherein none of any of the radicals $R_{10}$, $R_{12}$ and $R_9$ present are acid-sensitive protecting groups, thereby producing a compound of formula I in one step.

One group of compounds will now be described in detail. It will be appreciated that considerations that apply to this group may apply to the whole group of prostaglandins evisaged.

In accordance with the invention there are also provided new optically active compounds of formula I', or racemic compounds of this formula,

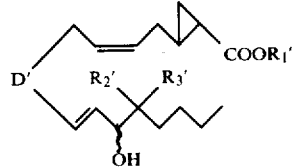

I' wherein

D' is one of the four carbocycles of formulae II'a, II'b, II'c or II'd,

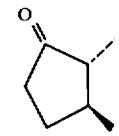

II'a

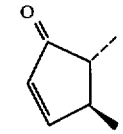

II'b

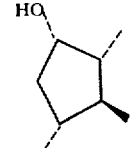

II'c

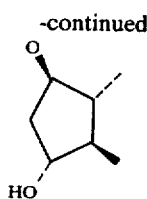
II'd

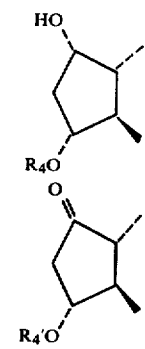
II'e

II'f

R'₁ is hydrogen or alkyl of 1 to 8 carbon atoms, cycloalkyl of 3 to 10 carbon atoms or aralkyl of 7 to 12 carbon atoms, and R'₂ and R'₃ independently are hydrogen or alkyl of 1 to 4 carbon atoms, The invention also includes pharmacologically acceptable salt forms of the compounds of formula I, when R'₁ is hydrogen.

In the cyclopentane formula II' the dotted connecting lines indicate that the substituents are linked with the cyclopentane ring in an α-configuration, i.e. they are situated below the level of the cyclopentane ring. The thicker solid connecting lines indicate that the substituents are linked with the cylopentane ring in a β-configuration, i.e. they are situated above the level of the cyclopentane ring. The wavy connecting line at C 15 in formula I' indicates that the hydroxyl group is present as an α- or β-configuration.

In regard to formula I' examples of alkyl groups of 1 to 8 carbon atoms are: methyl, ethyl, propyl, butyl, pentyl, hexyl, heptyl, octyl, including the isomeric forms of the same. Examples of cycloalkyl groups of 3 to 10 carbon atoms (including alkyl-substituted cycloalkyl groups) are: cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert.butylcyclopentyl, cyclohexyl, 4-tert.butylcyclohexyl, 3-isopropylcyclohexyl, 2,2-dimethylcyclohexyl, cycloheptyl, cyclooctyl, cyclononyl and cyclodecyl. Examples of aralkyl groups of 7 to 12 carbon atoms are: benzyl, phenethyl, 1-phenethyl, 2-phenylpropyl, 4-phenylbutyl, 3-phenylbutyl, 2-(1-naphthylethyl) and 1-(2-naphthylmethyl).

Further, in accordance with the invention a compound of formula I' may be obtained by a process comprising (a) removing any protective group present in a compound of formula III',

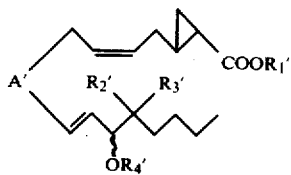
III' wherein
R'₁, R'₂ and R'₃ are as defined above,
R'₄ is trialkylsilyl or tetrahydropyranyl, and
A' is a carbocycle of formula II'a or II'b as defined above or of formula II'e or II'f.

(b) removing water from a compound of formula I'a,

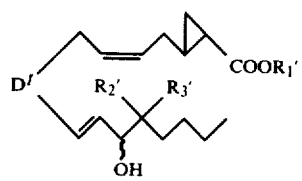
I'a wherein
D' is a carbocycle of formula II'd as defined above and
R'₁, R'₂ and R'₃ are as defined above to produce a compound of formula I'b,

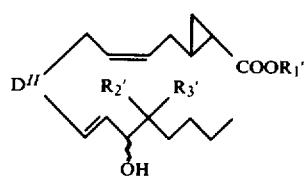
I'b wherein
D'' is a carbocycle of formula II'b as defined above and
R'₁, R'₂ and R'₃ are as defined above,
(c) hydrolysing a compound of formula I'c,

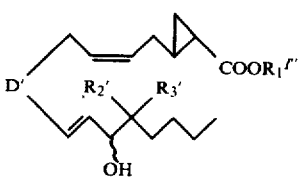
I'c wherein
R'''₁ is alkyl, cycloalkyl or aralkyl and
R'₂, R'₃ and D' are as defined above,
to produce a compound of formual I'd,

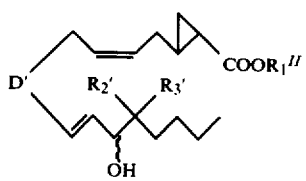
I'd wherein

R$^{II}_1$ is hydrogen and

R$'_2$, R$'_3$ and D' are as defined above, or (d) esterifying a compound of formula I'd as defined above to produce a compound of formula I'c.

Process variant (a) may be effected in conventional manner for the hydrolysis of tetrahydropyranyl or trialkylsilyl protecting groups in prostaglandins. For example the reaction may be carried out in solution, for example an organic acid/tetrahydrofuran/water mixture, e.g. acetic acid/tetrahydrofuran/water mixture.

A mineral acid is preferably present, e.g. hydrochloric acid conveniently in methanol, or sulphuric acid. The reaction is conveniently effected at from $-10°$ to $+150°$ C., preferably at from $30°$–$60°$ C.

The trialkylsilyl group preferably contains up to 6 carbon atoms in each alkyl group thereof, e.g. tert-butyl dimethylsilyl.

Process variant (b) may be effected in conventional manner for selectively dehydrating a 15-hydroxy prostaglandin E$_2$ to obtain a 15-hydroxy prostaglandin F$_{2\alpha}$.

Preferably a dilute aqueous acid solution is used, e.g. acetic acid. The reaction is preferably carried out at from 0° to 60°.

Process variant (c) may be effected in conventional manner for the hydrolysis of a prostaglandin ester to obtain a prostaglandin.

Process variant (d) may be effected in conventional manner for the esterification of a 15-hydroxy prostaglandin to produce a 15-hydroxy prostaglandin ester.

The starting materials for the process variant (a), the compounds of formula III'a,

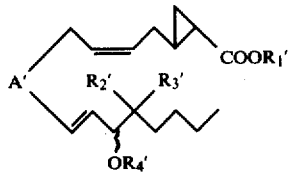

III'a wherein wherein R$'_1$ to R$'_4$ are as defined above, and

A' is one of the carbocycles II'a, II'b or II'f, are new and may be produced by oxidizing a compound of formula IV',

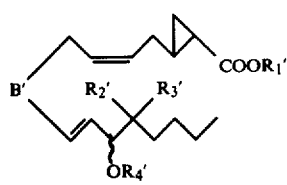

IV' wherein

R$'_1$ to R$'_4$ are as defined above, and

B' is respectively one of the carbocycles of formulae II'g or II'h,

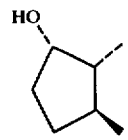

II'g

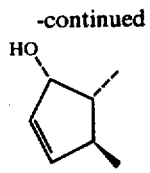

II'h or of formula II'e as defined above.

A suitable reagent for the oxidation is Collins reagent (pyridine/chromium trioxide), Jones reagent (CrO$_3$/H$^+$/acetone) or a sulphide reagent, e.g.

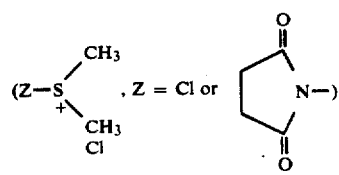

The reaction may be carried out in conventional manner for the oxidation of a prostaglandin having an 9-hydroxy group. An inert solvent is preferably used. In the case of the sulphide reagent the solvent may be for example toluene and a suitable reaction temperature is from $-30°$ to $-20°$ C. When a carboxylic acid is used as starting material, this is preferably protected in conventional manner when a sulphide reagent is used.

For the production of compounds of formula IIIa wherein B is the carbocycle II'b, the oxidation may also be effected with dichlorodicyanobenzoquinone or activated manganese dioxide.

The compounds of formula IV' are produced by, e.g. reacting a compound of formula V',

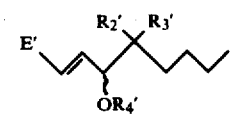

V' wherein

R$'_2$, R$'_3$ and R$'_4$ are as defined above, and

E' is one of the three carbocycles of formulae V'a, V'b or V'c,

V'a

V'b

-continued

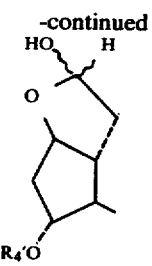

whereby the radical $R'_4$ in formula Vc has the above significance, with a compound of formula VI',

wherein $R'_1$ is as defined above, $R'_5$ is naphthyl or phenyl, each of which may be unsubstituted or preferably mono- or di-substituted by lower alkyl, e.g. of 1 to 4 carbon atoms, or lower alkyl, e.g. of 1 to 4 carbon atoms, and X' is chlorine, iodine or bromine.

As it will be appreciated that the compound of formula IV' wherein B is a carbocycle of formula II'e is the same as a compound of formula III' wherein A is a carbocycle of formula II'e, the present invention also provides a process for the production of a compound of formula III' wherein A is a carbocycle of formula II'e comprising reacting a compound of formula V' wherein E is a carbocycle of formula V'c with a compound of formula VI'.

The reaction is effected in accordance with known methods, for example by a Wittig reaction. The reaction is preferably effected in dimethyl sulphoxide or dimethylsulphoxide/tetrahydrofuran. A suitable temperature is between 20° to 80° C. conveniently room temperature.

The starting material, compounds of formula VI' wherein $R'_1$, $R'_5$ and X' are as defined above, are new and may be produced, for example, by reacting a 4-halogen-1-butene of formula VII', $$X'-CH_2-CH_2-CH=CH_2 \qquad VII'$$

wherein X' is chlorine, iodine or bromine, with a diazoacetic acid alkyl ester of formula VIII', $$N_2CH-COOR'_1 \qquad VIII'$$

wherein $R'_1$ is alkyl.

The resulting isomers of cyclopropanecarboxylic acid alkyl esters of formula IX',

wherein $R'_1$ and X' are as defined above, may be separated. The ester group may be hydrolysed, e.g. under conventional acid conditions. If desired the optical antipodes may be separated in conventional manner, e.g. through diastereoisomer salt formation, e.g. with optically active ephedrine. The optically active acid may be esterified in conventional manner and reacted with a phosphine compound of formula X',

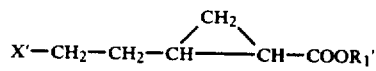

wherein $R'_5$ is as defined above. The phosphonium salt production may be effected in conventional manner, for example in an inert solvent, e.g. benzene. The reaction may be effected at the reflux temperature.

Free acid forms of compounds of formula I'd may be converted into salt form in conventional manner and vice versa. Compounds of formula I' may be in racemic form or in individual optical isomer form. Individual optical isomer forms may be obtained from racemic forms in conventional manner or by using appropriate starting materials in individual optical isomer form. It is preferred to separate the individual optical isomers of compounds of formula IX' as mentioned above.

Lower alkyl where not particularly defined otherwise preferably has up to 8 carbon atoms.

It will be appreciated that the cyclopropyl ring may be easily introduced by way of a Wittig reaction with a compound of formula

wherein

B is a reactive moiety capable of combining with an oxygen atom of a carbonyl group in a Wittig reaction, R is a group which is essentially inert in a Wittig reaction, or the corresponding Wittig salt.

B is, for example, $P(R'_5)_3$ as defined above.

$R_3$ is, for example, $R_9$ or R as defined above.

Insofar as the production of any starting materials is not particularly described, these compounds are known, or may be produced and purified in accordance with known processes, or in a manner analogous to processes described herein, e.g. in the Examples, or to known processes.

Free acid forms of compounds of formula I wherein $R_3$ is hydrogen may be converted into salt forms in conventional manner and vice versa. A suitable salt form is the sodium salt.

In the following Examples all temperatures are in degrees Centigrade and are uncorrected.

IR refers to characteristic bands observed with a methylene chloride solution (unless otherwise stated).

The nomenclature of the compounds is based on prostanoic acid with the five-membered ring on the left and the two side-chains on the right, or the related natural prostaglandin A, B, C, D, E, F, etc. The prefix "epi" donates that the configuration at the indicated carbon atom is opposite to the configuration at that carbon atim in prostanoic acid or the related natural prostaglandin.

Methano is the same as "methylene". (+) or (−)-cis or -trans-methylene (or methano) as used hereinafter refers to the respective (+)- or (−)- optical isomer of cis or trans-2-(2'-bromoethyl)cycloprop-1l-yl carboxylic acid or carboxylic acid ester, which may be used in the preparation of the corresponding compound of formula I according to conventional stereospecific procedures, e.g. those described hereinafter. The substituents of any 2,3-cyclopropyl group are trans to each other unless specifically mentioned otherwise.

Where the preparation of the example heading compounds is not particularly described, these are produced in analogous manner to that described in Example 1 of Group I.

It is to be appreciated that unless otherwise stated the exemplified prostaglandins are in optically active form corresponding to that of prostanoic acid or the natural prostaglandin referred to. However, the racemic compounds are also preparable in the same way.

GROUP I

EXAMPLE 1

2,3-trans-methano-prostaglandin $F_{2\alpha}$ [process variant (a)]

40 mg of 2,3-methano-trans-11,15-bistetrahydropyranyl-prostaglandin $F_{2\alpha}$ are dissolved in 2 cc of a mixture of acetic acid, tetrahydrofuran, water (3:1:1) and the solution is heated to 60° for 2 hours.

After concentrating by evaporation at reduced pressure, the residue is separated on 3 g of silica gel with chloroform containing 17% of methanol, whereby the pure title compound is obtained. M.P. 108°–112°.

NMR (CDCl$_3$, 90 megacycles per second) inter alia signals at:

| 4 H (m) | 5.45 | ppm | vinyl protons |
|---|---|---|---|
| 3 H | 3.8–4.2 | ppm | CH—OH |
| 3 H (t) | 0.9 | ppm | methyl |

2,3-cis-methano-prostaglandin $F_{2\alpha}$ and the following esters are produced in analogous manner:
2,3-cis-methano-prostaglandin $F_{2\alpha}$ methyl ester,
2,3-trans-methano-prostaglandin $F_{2\alpha}$ methyl ester,
2,3-trans-methano-prostaglandin $F_{2\alpha}$ ethyl ester,
2,3-cis-methano-prostaglandin $F_{2\alpha}$ ethyl ester,
2,3-trans-methano-prostaglandin $F_{2\alpha}$ benzyl ester,
2,3-cis-methano-prostaglandin $F_{2\alpha}$ benzyl ester.

The 2,3-trans-methano-11,15-bis-tetrahydropyranyl-prostaglandin $F_{2\alpha}$, used as starting material, is produced as follows:

(a) 2-bromoethyl-cyclopropane-carboxylic acid ethyl ester 40 cc of diazo-acetic acid ethyl ester are slowly added dropwise, while stirring vigorously, to a suspension heated to 100° of 2.48 g of copper powder in 22 g of 4-bromo-1-butene. After 2 hours at 100°, filtration is effected and the isomeric cyclopropylcarboxylic acid esters are separated by chromatography on 900 g of silica gel with benzene as eluant.

trans-cyclopropane-1-(2-bromoethyl)-2-carboxylic acid ethyl ester

IR (methylene chloride) inter alia bands at: 1710, 1420, 1200, 1180 cm$^{-1}$.

NMR (CDCl$_3$, 60 megacycles per second) inter alia signals at:

| 2 H 4.17 ppm | (O—CH$_2$—CH$_3$) |
|---|---|
| 2 H 3.45 ppm | (—CH$_2$—CH$_2$—Br) |
| 3 H 1.25 ppm | (CH$_3$—CH$_2$—) |
| M$^+$ = 220 | | cis-cyclopropane-1-(2-bromoethyl)-2-carboxylic acid ethyl ester

IR (methylene chloride) inter alia bands at: 1715, 1395, 1180 cm$^{-1}$.

NMR (CDCl$_3$, 60 megacycles per second) inter alia signals at:

| 2 H 4.16 ppm | (O—CH$_2$—CH$_3$) |
|---|---|
| 2 H 3.42 ppm | (—CH$_2$—CH$_2$—Br) |
| 2 H 2.15 ppm | (—CH$_2$—CH$_2$—CH) |
| 3 H 1.28 ppm | (CH$_3$—CH$_2$—) |
| M$^+$ = 220 | |

(b) trans-cyclopropane-1-(2-bromoethyl)-2-carboxylic acid 1 g of trans-cyclopropane-1-(2-bromoethyl)-2-carboxylic acid ethyl ester is added to a mixture cooled to 0° of 6.4 cc of 33% hydrobromic acid and 1.7 cc of concentrated sulphuric acid while stirring vigorously. After one hour at room temperature, the solution is heated to 100° for 15 minutes. The cooled solution is poured on 60 cc of a cold, saturated ammonium sulphate solution and is extracted thrice with methylene chloride; the combined extracts are washed with water, dried and concentrated by evaporation at reduced pressure. The residue is separated on 40 g of silica gel with chloroform containing 1% of methanol (50 cc fractions), whereby the title compound is obtained.

IR (methylene chloride) inter alia bands at: 3450 - 2700, 1700, 1460, 1215 cm$^{-1}$.

NMR (CDCl$_3$, 60 megacycles per second) inter alia signals at:

| 1 H 10.5 ppm | (—COOH) |
|---|---|
| 2 H 3.42 ppm | (—CH$_2$—CH$_2$—Br) |
| 2 H 1.83 ppm | (CH—CH$_2$—CH$_2$—) |
| M$^+$ = 193 | | cis-cyclopropane-1-(2-bromoethyl)-2-carboxylic acid

Treatment as described above yields the corresponding cis-cyclopropane-1-(2-bromoethyl)-2-carboxylic acid.

IR (methylene chloride) inter alia bands at: 3450 - 2470, 1695, 1220 cm$^{-1}$.

NMR (CDCl$_3$, 60 megacycles per second) inter alia signals at:

| 9.5 ppm | (1 H) | —COOH |
|---|---|---|
| 3.47 ppm | (2 H) | CH$_2$—Br |
| 2.18 ppm | (2 H) | —CH$_2$— | trans-cyclopropane-1-(2-bromoethyl)-2-carboxylic acid methyl ester 200 mg of the trans acid are dissolved in 10 cc of methanol and treated with a solution of diazomethane in ether at room temperature (20°). After removing the solvent at reduced pressure, the residue (200 mg) is chromatographed on silica gel with benzene whereby the corresponding methyl ester is obtained.

IR (methylene chloride) inter alia bands at: 1720, 1210, 1120 cm$^{-1}$.

NMR (CDCl$_3$, 100 megacycles per second) inter alia signals at:

| 3 H | 3.68 ppm | COOCH$_3$ |
|---|---|---|
| 2 H | 3.45 (t) | CH$_2$—Br |

| -continued | | |
|---|---|---|
| 2 H | 1.9 (m) | CH₂—CH₂—Br |

The same compound is obtained by treating the trans acid with 3-methyl-1-p-tolyl-triazine.

The following esters are produced in analogous manner:
cis-cyclopropane-1-(2-bromoethyl)-2-carboxylic acid methyl ester,
trans-cyclopropane-1-(2-bromoethyl)-2-carboxylic acid ethyl ester,
cis-cyclopropane-1-(2-bromoethyl)-2-carboxylic acid ethyl ester,
trans-cyclopropane-1-(2-bromoethyl)-2-carboxylic acid benzyl ester,
cis-cyclopropane-1-(2-bromoethyl)-2-carboxylic acid benzyl ester.

(c) triphenyl-phosphonium salt of ethyl-trans-cyclopropane-carboxylic acid 10 g of triphenyl phosphine are added to 5 g of (±)-trans-cyclopropane-1-(2-bromoethyl)-2-carboxylic acid in 100 cc of absolute benzene and the mixture is boiled at reflux for 42 hours. After removing the solvent at reduced pressure, the residue is separated on 600 g of silica gel with mixtures of chloroform/methanol/acetic acid (300 cc fractions), whereby the title compound is obtained.

IR (methylene chloride) inter alia bands at: 3400 - 3000, 1725, 1440, 1115 cm⁻¹.

NMR (CDCl₃, 60 megacycles per second) inter alia signals at:

| 15 H | 7.75 ppm | (aromatic H) |
|---|---|---|
| 2 H | 3.8 ppm | (CH₂—P—) |

The phosphonium salts of the following compounds are produced in analogous manner:
ethyl-cis-cyclopropane-carboxylic acid,
ethyl-trans-cyclopropane-carboxylic acid ethyl ester,
ethyl-cis-cyclopropane-carboxylic acid ethyl ester,
ethyl-trans-cyclopropane-carboxylic acid methyl ester,
ethyl-cis-cyclopropane-carboxylic acid methyl ester,
ethyl-trans-cyclopropane-carboxylic acid benzyl ester,
ethyl-cis-cyclopropane-carboxylic acid benzyl ester.

(d) 2,3-trans-methano-11,15-bis-tetrahydropyranyl-prostaglandin F$_{2\alpha}$ [Wittig reaction]

70 mg of sodium hydride are dissolved in 0.7 cc of dimethyl sulphoxide and the solution is kept at 75° for 40 minutes in an atmosphere of nitrogen. After cooling, the triphenyl-phosphonium salt of (±) -ethyl-trans-cyclopropane-carboxylic acid in 1 cc of absolute dimethyl sulphoxide is added to the brown solution. Stirring is then effected at room temperature for 1½ hours and 145 mg of 2β-(3'α-tetrahydropyranyloxy-1'-trans-octenyl)-5α-hydroxy-3α-tetrahydropyranyloxy-cyclopentane-acetaldehyde lactol are subsequently added to 1.2 cc of the above solution. The reaction mixture is allowed to stand at room temperature for 15 minutes, is heated to 75° for 3 hours, is subsequently poured on 20 g of ice, the pH is carefully adjusted to 3 and extraction is effected with methylene chloride. Chromatography on 20 g of silica gel with chloroform containing 2% of methanol yields the title compound in pure form.

IR (methylene chloride) inter alia bands at: 3500, 1710 cm⁻¹.

NMR (CDCl₃, 90 megacycles per second) inter alia signals at:

| 4 H (m) | 5.4 ppm |
|---|---|
| 2 H | 4.7 ppm |
| 3 H (t) | 0.9 ppm |

The following compounds are produced in analogous manner:
2,3-cis-methano-11,15-bis-tetrahydropyranyl-prostaglandin F$_{2\alpha}$,
2,3-trans-methano-11,15-bis-tetrahydropyranyl-prostaglandin F$_{2\alpha}$ methyl ester,
2,3-cis-methano-11,15-bis-tetrahydropyranyl-prostaglandin F$_{2\alpha}$ methyl ester,
2,3-trans-methano-11,15-bis-tetrahydropyranyl-prostaglandin F$_{2\alpha}$ ethyl ester,
2,3-cis-methano-11,15-bis-tetrahydropyranyl-prostaglandin F$_{2\alpha}$ ethyl ester,
2,3-trans-methano-11,15-bis-tetrahydropyranyl-prostaglandin F$_{2\alpha}$ benzyl ester,
2,3-cis-methano-11,15-bis-tetrahydropyranyl-prostaglandin F$_{2\alpha}$ benzyl ester,
whereby the esters may alternatively be obtained directly from the corresponding acids.

EXAMPLE 2

16,16-dimethyl-2,3-trans(+)-methano-prostaglandin F$_{2\alpha}$ [process variant a)]

200 mg of 16,16-dimethyl-2,3-(+)-methano-11,15-bis-tetrahydropyranyl-prostaglandin F$_{2\alpha}$ are dissolved in 7 cc of a mixture of acetic acid, tetrahydrofuran, water (3:1:1) and kept at 40° for 5 hours. After concentrating by evaporation at reduced pressure, the residue is chromatographed on 23 g of silica gel with chloroform containing 7% of methanol, whereby the crude title compound is obtained.

$[\alpha]_D^{20} = +88°$ (c = 1.01, CHCl₃).

IR (methylene chloride) inter alia bands at 3600-3400, 1695 cm⁻¹.

NMR (CDCl₃, 100 megacycles per second) inter alia bands at:

| 4 H | ~5.5 ppm | vinyl H |
|---|---|---|
| 6 H | ~4 ppm | 3 × CH—OH |
| 6 H | 1.28 ppm | 2 × CH₃—C |

The following compounds are produced in analogous manner:
16,16-dimethyl-2,3-trans(+)-methano-prostaglandin F$_{2\alpha}$ methyl ester,
16,16-dimethyl-2,3-trans(+)-methano-prostaglandin F$_{2\alpha}$ ethyl ester,
16,16-dimethyl-2,3-trans(+)-methano-prostaglandin F$_{2\alpha}$ benzyl ester,
2,3-trans(+)-methano-prostaglandin F$_{2\alpha}$,
2,3-trans(+)-methano-prostaglandin F$_{2\alpha}$ methyl ester,
2,3-trans(+)-methano-prostaglandin F$_{2\alpha}$ ethyl ester,
2,3-trans(+)-methano-prostaglandin F$_{2\alpha}$ benzyl ester.

The 16,16-dimethyl-2,3-trans(+)-methano-11,15-bis-tetrahydropyranyl-prostaglandin F$_{2\alpha}$, used as starting material, is produced as follows:

(a) (+)-trans-cyclopropane-1-(2-bromoethyl)carboxylic acid 29 g of (−)-ephedrine in 200 cc of methylene chloride are added to 66 g of trans-cyclopropane-1-(2-bromoethyl)carboxylic acid in 200 cc of methylene chloride and the mixture is allowed to stand at 20° for 2½ hours. Upon adding n-hexane crystals are formed. Filtration and recrystallization from methylene chloride/hexane and methylene chloride/ethyl acetate are effected.

M.P. 125°–126°; $[\alpha]_D^{20} = +22°$ (c=1.26, CHCl$_3$).

Extraction with methylene chloride/dilute hydrochloric acid yields the (+) acid: $[\alpha]_D^{20} = +75.3°$ (c=1.94, CHCl$_3$).

The acid is converted into the following esters as described in Example 1:
(+)-trans-cyclopropane-1-(2-bromoethyl)carboxylic acid methyl ester,
(+)-trans-cyclopropane-1-(2-bromoethyl)carboxylic acid ethyl ester,
(+)-trans-cyclopropane-1-(2-bromoethyl)carboxylic acid benzyl ester.

(b) triphenylphosphonium salt of (+)-trans-cyclopropane-1-(2-bromoethyl)carboxylic acid 10.3 g of triphenylphosphine are added to 6.3 g of (+)-trans-cyclopropane-1-(2-bromoethyl)carboxylic acid in 150 cc of absolute benzene and the mixture is boiled at reflux for 65 hours. After cooling, the precipitated crystals are filtered off.

M.P. 121°–125°; $[\alpha]_D^{20} = +17.5°$ (c=1.18, CHCl$_3$).

IR and NMR spectra correspond to those of the racemic compound.

The phosphonium salts of the following compounds are produced in analogous manner:
ethyl-trans(+)-cyclopropane-carboxylic acid methyl ester,
ethyl-trans(+)-cyclopropane-carboxylic acid ethyl ester,
ethyl-trans(+)-cyclopropane-carboxylic acid benzyl ester.

(c) 16,16-dimethyl-2,3-trans(+)-methano-11,15-bis-tetrahydropyranyl-prostaglandin F$_{2\alpha}$ [Wittig reaction]

600 mg of sodium hydride are dissolved in 6 cc of absolute dimethyl sulphoxide and kept at 75° in an atmosphere of nitrogen for 55 minutes. After cooling, 2.1 cc of this solution are slowly added dropwise to a prepared solution of 1.95 g of the triphenylphosphonium salt of (+)-trans-cyclopropane-1-(2-bromoethyl)carboxylic acid in 5 cc of absolute dimethyl sulphoxide and the mixture is stirred in an atmosphere of nitrogen for 45 minutes.

4.5 cc of the ylide solution described above are added at 20° to a prepared solution of 1 g of 2β-(4′,4′-dimethyl-3′α-tetrahydropyranyloxy-1′-transoctenyl)-5α-hydroxy-3α-tetrahydropyranyloxy-cyclopentane-acetaldehyde lactol in 1 cc of absolute dimethyl sulphoxide and the mixture is kept at 60° for 50 minutes. After the addition of a further 4.5 cc of the ylide solution, stirring is again effected at 60° for one hour. The cooled reaction mixture is poured on ice, the pH of the aqueous phase is adjusted to 3–5 and extraction is effected thrice with methylene chloride. The resulting crude product is chromatographed on 140 g of silica gel with chloroform containing 1 to 5% of methanol, whereby the pure title compound is obtained. $[\alpha]_D^{20} = +35.5°$ (c=1.07, CHCl$_3$).

IR (methylene chloride) inter alia bands at 3500, 1695 cm$^{-1}$.

NMR (CDCl$_3$, 90 megacycles per second) inter alia signals at:

| 4 H | ~5.5 ppm | vinyl H |
|---|---|---|
| 2 H | 4.6 ppm | THP H |

The following compounds are produced in analogous manner:
16,16-dimethyl-2,3-trans(+)-methano-11,15-bis-tetrahydropyranyl-prostaglandin F$_{2\alpha}$ methyl ester,
16,16-dimethyl-2,3-trans(+)-methano-11,15-bis-tetrahydropyranyl-prostaglandin F$_{2\alpha}$ ethyl ester,
16,16-dimethyl-2,3-trans(+)-methano-11,15-bis-tetrahydropyranyl-prostaglandin F$_{2\alpha}$ benzyl ester.

When the Wittig reaction is effected with 2α-(3′α-tetrahydropyranyloxy-1′-trans-octenyl)-5α-hydroxy-3α-tetrahydropyranyloxy-cyclopentaneacetaldehyde lactol, then the following compounds are produced in analogous manner:
2,3-trans(+)-methano-11,15-bis-tetrahydropyranyl-prostaglandin F$_{2\alpha}$,
2,3-trans(+)-methano-11,15-bis-tetrahydropyranyl-prostaglandin F$_{2\alpha}$ methyl ester,
2,3-trans(+)-methano-11,15-bis-tetrahydropyranyl-prostaglandin F$_{2\alpha}$ ethyl ester,
2,3-trans(+)-methano-11,15-bis-tetrahydropyranyl-prostaglandin F$_{2\alpha}$ benzyl ester.

EXAMPLE 3

16,16-dimethyl-2,3-trans(+)-methano-prostaglandin E$_2$ [prostoglandin acid group protection; oxidation; process varient (a)]

100 mg of 16,16-dimethyl-2,3-trans(+)-methano-11,15-bis-tetrahydropyranyl-prostaglandin F$_{2\alpha}$ are dissolved in 1 cc of absolute toluene, and 26.7 mg of tert.butyl dimethylchlorosilane are added in an atmosphere of nitrogen. The reaction solution is cooled to 0°, 18 mg of triethylamine are added, stirring is effected at 20° for 2½ hours, the solution is cooled to −30° and slowly added dropwise to a solution of 108 mg of N-chlorosuccinimide in 4 cc of absolute toluene and 60 mg of dimethyl sulphide within 35 minutes. After a further 2¾ hours at −20°, 220 mg of triethylamine in 1 cc of pentane are added dropwise and working up is effected with ether/water for a further 10 minutes. The residue (100 mg) is chromatographed on 8 g of silica gel with chloroform containing 2% of methanol. 16,16-dimethyl-2,3-trans(+)-methano-11,15-bis-tetrahydropyranyl-prostaglandin E$_2$ tert.butyl dimethylsilyl ester is obtained.

IR (methylene chloride) inter alia bands at 1735, 1695 cm$^{-1}$.

50 mg of the ester described above are dissolved in 0.7 cc of acetone, 0.2 cc of water are added dropwise, and 0.25 cc of a solution of 246 mg of sodium acetate in 3 cc of acetone, 1 cc of water and 180 mg of acetic acid are added at 0°. Stirring is effected at 0° for 45 minutes, and at 25° for 1¼ hours, and subsequently working up is effected with ether.

The residue is dissolved in 2 cc of acetic acid/water/tetrahydrofuran (3:1:1) and kept at 38° for 2½ hours. After concentrating by evaporation at reduced pressure, the residue is chromatographed on 2.5 g of silica gel with chloroform containing 3% of methanol. The pure title compound is obtained.

IR (methylene chloride) inter alia bands at 1735, 1695 cm$^{-1}$.

NMR (CDCl$_3$, 90 megacycles per second) inter alia signals at:

| 4 H | 5.3–5.8 ppm | (vinyl protons) |
|---|---|---|
| 5 H | 3.7–4.2 ppm | 2 × —CH—OH + —COOH |

2,3-trans(+)-methano-prostaglandin E$_2$ is produced in analogous manner.

The following compounds are produced in analogous manner, using the esters described in Example 2 as starting materials:

16,16-dimethyl-2,3-trans(+)-methano-prostaglandin E$_2$ methyl ester,
16,16-dimethyl-2,3-trans(+)-methano-prostaglandin E$_2$ ethyl ester,
16,16-dimethyl-2,3-trans(+)-methano-prostaglandin E$_2$ benzyl ester,
2,3-trans(+)-methano-prostaglandin E$_2$ methyl ester,
2,3-trans(+)-methano-prostaglandin E$_2$ ethyl ester,
2,3-trans(+)-methano-prostaglandin E$_2$ benzyl ester.

EXAMPLE 4

16,16-dimethyl-2,3-trans(−)-methano-prostaglandin F$_{2\alpha}$ [process variant (a)]

109 mg of 16,16-dimethyl-2,3-trans(−)-methano-11,15-bis-tetrahydropyranyl-prostaglandin F$_{2\alpha}$ are dissolved in 3.5 cc of a mixture of acetic acid/tetrahydrofuran/water (3:1:1) and kept at 40° for 6 hours. After concentrating by evaporation at reduced pressure, the residue is chromatographed on 5 g of silica gel with chloroform containing 7% of methanol, whereby the pure title compound is obtained.

$[\alpha]_D^{20} = +13.8°$ (c = 1.02, CHCl$_3$).

IR (methylene chloride) inter alia bands at 3600, 3400, 1695 cm$^{-1}$.

NMR (CDCl$_3$, 90 megacycles per second) inter alia signals at:

| 4 H | 5.3–5.7 ppm | vinyl-H |
|---|---|---|
| 7 H | 3.9–4.3 ppm | 3 × ⟩CH—OH + COOH |
| | 1.28 ppm | CH$_3$⟩⟨CH$_3$ |

The following compounds are produced in analogous manner:

16,16-dimethyl-2,3-trans(−)-methano-prostaglandin F$_{2\alpha}$ methyl ester,
16,16-dimethyl-2,3-trans(−)-methano-prostaglandin F$_{2\alpha}$ ethyl ester,
16,16-dimethyl-2,3-trans(−)-methano-prostaglandin F$_{2\alpha}$ benzyl ester,
2,3-trans(−)-methano-prostaglandin F$_{2\alpha}$,
2,3-trans(−)-methano-prostaglandin F$_{2\alpha}$ methyl ester,
2,3-trans(−)-methano-prostaglandin F$_{2\alpha}$ ethyl ester,
2,3-trans(−)-methano-prostaglandin F$_{2\alpha}$ benzyl ester.

The 16,16-dimethyl-2,3-trans(−)-methano-11,15-bis-tetrahydropyranyl-prostaglandin F$_{2\alpha}$, used as starting material, is produced as follows:

(a) (−)-trans-cyclopropane-1-(2-bromoethyl)carboxylic acid

The title compound is obtained in a manner analogous to that described in Example 2 (a) with (+)-ephedrine.

$[\alpha]_D^{20} = -75.0°$ (c = 1.56, CHCl$_3$).

The spectroscopic data of the title compound are identical with those of the (+)-acid.

The acid is converted into the following esters in a manner analogous to that described in Example 1:

(−)-trans-cyclopropane-1-(2-bromoethyl)carboxylic acid methyl ester,
(−)-trans-cyclopropane-1-(2-bromoethyl)carboxylic acid ethyl ester,
(−)-trans-cyclopropane-1-(2-bromoethyl)carboxylic acid benzyl ester.

(b) Triphenylphosphonium salt of (−)-trans-cyclopropane-1-(2-bromoethyl)carboxylic acid 10 g of triphenylphosphine are added to 61 g of (−)-trans-cyclopropane-1-(2-bromoethyl)carboxylic acid in 200 cc of absolute benzene, and the mixture is boiled at reflux for 63 hours. After cooling the precipitated crystals are filtered off.

M.P. 120°–122°, $[\alpha]_D^{20} = -17.3°$ (c = 1.19, CHCl$_3$).

The IR and NMR spectra correspond to those of the enantiomorphic compounds.

The phosphonium salts of the following compounds are produced in analogous manner:

ethyl-trans(−)-cyclopropane-carboxylic acid methyl ester,
ethyl-trans(−)-cyclopropane-carboxylic acid ethyl ester,
ethyl-trans(−)-cyclopropane-carboxylic acid benzyl ester.

(c) 16,16-dimethyl-2,3-trans(−)-methano-11,15-bis-tetrahydropyranyl-prostaglandin F$_{2\alpha}$ [Wittig reaction]

300 mg of sodium hydride are suspended in 3 cc of absolute dimethyl sulphoxide, and the suspension is kept at 75° for 45 minutes in an atmosphere of nitrogen. After cooling, 0.9 cc of this solution are slowly added dropwise to a prepared solution of 1 g of the triphenylphosphonium salt of (−)-trans-cyclopropane-1-(2-bromoethyl)carboxylic acid in 2.5 cc of absolute dimethyl sulphoxide, and the mixture is stirred for 45 minutes under nitrogen.

1.9 cc of the ylide solution described above are slowly added dropwise to a solution of 500 mg of 2β-(4',4'-dimethyl-3'α-tetrahydropyranyloxy-1'-trans-octenyl)-5α-hydroxy-3α-tetrahydropyranyloxy-cyclopentane acetaldehyde lactol in 0.6 cc of absolute tetrahydrofuran. After 40 minutes at 60°, a further 1.9 cc of the ylide solution are added dropwise and the mixture is kept at 60° for a further hour. The cooled reaction mixture is poured on 100 g of ice, the pH of the aqueous phase is adjusted to 3–4 and the aqueous phase is extracted thrice with methylene chloride. The resulting crude product is purified by chromatography on 40 g of silica gel, whereby the title compound is obtained with chloroform containing 2% of methanol.

IR (methylene chloride) inter alia bands at 3500, 1695 cm$^{-1}$.

The following compounds are produced in analogous manner:

16,16-dimethyl-2,3-trans(−)-methano-11,15-bis-tetrahydropyranyl-prostaglandin F$_{2\alpha}$ methyl ester,
16,16-dimethyl-2,3-trans(−)-methano-11,15-bis-tetrahydropyranyl-prostaglandin F$_{2\alpha}$ ethyl ester,
16,16-dimethyl-2,3-trans(−)-methano-11,15-bis-tetrahydropyranyl-prostaglandin F$_{2\alpha}$ benzyl ester.

When the Wittig reaction is effected with 2β-(3'α-tetrahydropyranyloxy-1'-trans-octenyl)-5α-hydroxy-3α-tetrahydropyranyloxy-cyclopentane acetaldehyde lactol, the following compounds are produced in analogous manner:

2,3-trans(−)-methano-11,15-bis-tetrahydropyranyl-prostaglandin F$_{2\alpha}$,
2,3-trans(−)-methano-11,15-bis-tetrahydropyranyl-prostaglandin F$_{2\alpha}$ methyl ester,
2,3-trans(−)-methano-11,15-bis-tetrahydropyranyl-prostaglandin F$_{2\alpha}$ ethyl ester,
2,3-trans(−)-methano-11,15-bis-tetrahydropyranyl-prostaglandin F$_{2\alpha}$ benzyl ester.

EXAMPLE 5

16,16-dimethyl-2,3-trans(−)-methano-prostaglandin E$_2$
[prostaglandin acid group protection; oxidation; process variant (a)]

177 mg of 16,16-dimethyl-2,3-trans(−)-methano-11,15-bis-tetrahydropyranyl-prostaglandin F$_{2\alpha}$ are dissolved in 1.5 cc of absolute toluene. A solution of 47.2 mg of tert.butyldimethyl chlorosilane in toluene is added dropwise in an atmosphere of nitrogen. The reaction solution is cooled to 0°, 32 mg of triethylamine are added and stirring is effected at 20° for 2½ hours. The reaction mixture is cooled to −30° and is slowly added dropwise to a solution of 191 mg of N-chlorosuccinimide in 6 cc of absolute toluene and 106.3 mg of dimethyl sulphide. After 2 hours at −30°/−20° 300 mg of triethylamine in 1 cc of pentane are added, stirring is continued for 10 minutes and working up is effected with ether/water. The residue (192 mg) is chromatographed on 12 g of silica gel with chloroform containing 1% of methanol.

The resulting silyl ester (IR in methylene chloride inter alia bands at 1735, 1675 cm$^{-1}$) is dissolved in 2.7 cc of acetone. 0.9 cc of water and 1.2 cc of a solution of 246 mg of sodium acetate in 3 cc of acetone, 1 cc of water and 180 mg of acetic acid are added to the solution which has been cooled to 0°. The reaction mixture is stirred at 0° for 30 minutes, at 25°-30° for 1½ hours, and is subsequently worked up with ether. The residue (IR in methylene chloride inter alia bands at 3500, 1735, 1695 cm$^{-1}$) is dissolved in 3 cc of acetic acid/water/tetrahydrofuran (3:1:1) and stirred at 40° for 6 hours. After concentrating by evaporation at reduced pressure, the residue is chromatographed on 4.5 g of silica gel with chloroform containing 2% of methanol. The pure title compound is obtained.

IR (methylene chloride) inter alia bands at 3600, 3400, 1735, 1695 cm$^{-1}$.

NMR (CDCl$_3$, 90 megacycles per second) inter alia signals at about:

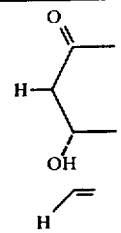

2,3-trans(−)-methano-prostaglandin E$_2$ is produced in analogous manner.

The following compounds are produced in analogous manner, using the esters described in Example 4 as starting materials:

16,16-dimethyl-2,3-trans(−)-methano-prostaglandin E$_2$ methyl ester,
16,16-dimethyl-2,3-trans(−)-methano-prostaglandin E$_2$ ethyl ester,
16,16-dimethyl-2,3-trans(−)-methano-prostaglandin E$_2$ benzyl ester,
2,3-trans(−)-methano-prostaglandin E$_2$ methyl ester,
2,3-trans(−)-methano-prostaglandin E$_2$ ethyl ester,
2,3-trans(−)-methano-prostaglandin E$_2$ benzyl ester.

EXAMPLE 6

16,16-dimethyl-2,3-trans(+)-methano-prostaglandin A$_2$
[process variant (b)]

50 mg of 16,16-dimethyl-2,3-trans(+)-methano-prostaglandin E$_2$ of Example 3 are dissolved in 2 cc acetic acid/water (9:1) and kept at 60° for 5½ hours. After the addition of toluene, concentration is effected by evaporation at reduced pressure and the residue is chromatographed on 0.5 g of silica gel with chloroform containing 0.5% of methanol. The pure title compound has the following characteristics:

IR (methylene chloride) inter alia bands at 3600, 1700, 1690, 1140 cm$^{-1}$.

NMR (CDCl$_3$, 90 megacycles per second) inter alia signals at:

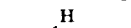
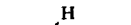

The following compounds are produced in analogous manner:

16,16-dimethyl-2,3-trans(+)-methano-prostaglandin A$_2$,
16,16-dimethyl-2,3-trans(+)-methano-prostaglandin A$_2$ methyl ester,
16,16-dimethyl-2,3-trans(+)-methano-prostaglandin A$_2$ ethyl ester,
16,16-dimethyl-2,3-trans(+)-methano-prostaglandin A$_2$ benzyl ester,
2,3-trans(+)-methano-prostaglandin A$_2$,
2,3-trans(+)-methano-prostaglandin A$_2$ methyl ester,
2,3-trans(+)-methano-prostaglandin A$_2$ ethyl ester,
2,3-trans(+)-methano-prostaglandin A$_2$ *benzyl ester*.

EXAMPLE 7

16,16-dimethyl-2,3-trans(−)-methano-prostaglandin A₂ [process variant (b)]

120 mg of 16,16-dimethyl-2,3-trans(−)-methano-prostaglandin E₂ of Example 5 are dissolved in 5 cc of acetic acid/water (9:1) and kept at 55°–60° for 15 hours. The reaction mixture is concentrated by evaporation at reduced pressure and the residue is chromatographed on 5 g of silica gel. The pure title compound is isolated with a mixture of chloroform/methanol.

IR (methylene chloride) inter alia bands at 3600, 1700, 1690, 1590, 1065, 1030 cm⁻¹.

NMR (CDCl₃, 90 megacycles per second) inter alia signals at:

| | | |
|---|---|---|
| 1 H 7.5 ppm | H | |
| 5 H 5.2–6.3 ppm | $\diagup\diagdown$=O | |
| 0.7–0.95 ppm | CH₃— | H |

The following compounds are produced in analogous manner:

16,16-dimethyl-2,3-trans(−)-methano-prostaglandin A₂,
16,16-dimethyl-2,3-trans(−)-methano-prostaglandin A₂ methyl ester,
16,16-dimethyl-2,3-trans(−)-methano-prostaglandin A₂ ethyl ester,
16,16-dimethyl-2,3-trans(−)-methano-prostaglandin A₂ benzyl ester,
2,3-trans(−)-methano-prostaglandin A₂,
2,3-trans(−)-methano-prostaglandin A₂ methyl ester,
2,3-trans(−)-methano-prostaglandin A₂ ethyl ester,
2,3-trans(−)-methano-prostaglandin A₂ benzyl ester.

Using the process described in Example 1 there is obtained the following compound:
2,3-trans(+)-methano-15-epi-prostaglandin DHA₂ napthylethylester.

GROUP II

EXAMPLE 1

16,16-dimethyl-9α-11α-15β-trihydroxy-2,3-(+)-methano-prosta-5cis,13trans-dienic acid 230 mg of 16,16-dimethyl-9α-hydroxy-11α-15β-bis-tetrahydro-pyranyloxy-2,3-(+)-methano-prosta-5cis,13trans-dienic acid are dissolved in 15 cc of a mixture of acetic acid, tetrahydrofuran, water (3:1:1) and the solution is allowed to stand at room temperature for 42 hours. After concentrating by evaporation at reduced pressure, the residue is chromatographed on 14 g of silica gel with chloroform+4% of methanol, whereby the pure title compound is obtained.

Thin layer chromatography: benzene, dioxane, acetic acid (20:10:1) Rf=0.52.

IR (methylene chloride) inter alia bands at: 3600, 3500, 1710-1695 cm⁻¹.

NMR (CDCl₃) inter alia signals at:

| 4 H | approx. 5.5 ppm | vinyl H |
|---|---|---|
| 3 H | approx. 4 ppm | 3 × CHOH |

The 16,16-dimethyl-9α-hydroxy-11α-15β-bis-tetrahydro-pyranyloxy-2,3-(+)-methano-prosta-5cis,13-trans-dienic acid, used as starting material, is produced as follows:

(a)

5α-hydroxy-2β-(3'-oxo-4',4'-dimethyl-trans-1-octenyl)-3α-p-phenyl-benzoyloxy-1α-cyclopentane-acetic acid-γ-lactone A solution of 124.8 g of dimethyl-2-oxo-3,3-dimethyl-heptyl-phosphonate in 170.3 cc of absolute dimethoxyethane is added to a cold (5°) suspension of 11.35 g of sodium hydride in 994.5 cc of absolute dimethoxyethane while stirring. The mixture is stirred at 20° for one hour, the clear yellow solution is cooled to −18°, and a solution cooled to 0° of the optically active aldehyde (2β-carboxaldehyde-5α-hydroxy-3α-p-phenyl-benzoyloxy-cyclopentane-acetic acid-γ-lactone) in 2109 cc of absolute dimethoxyethane is subsequently added. After 2 hours at approx. 0°, the reaction mixture is again cooled to about −15° and the pH is adjusted to 6 by the dropwise addition of acetic acid. The solvent is then removed by distillation in a vacuum, 2 liters of petroleum ether are added to the residue (201.6 g yellow-brown oil), whereby white crystals precipitate over night. M.P. 100°–101.5°.

(b)

5α-hydroxy-2β-(3'-hydroxy-4',4'-dimethyl-trans-1-octenyl)-3α-p-phenylbenzoyl-1α-cyclopentane-acetic acid A solution of 53.6 g of ketone (Example 1a) in 281 cc of absolute dimethoxyethane is added dropwise within 5 minutes to 734.6 cc of a mixture cooled to −18° of zinc borohydride/dimethoxyethane (1 cc contains 28.7 mg of zinc borohydride). Stirring is effected for 3½ hours at 2°–5° and for a further 45 minutes at 5°–10°. Cooling is then effected to −15° and the pH is adjusted to 6 with a 10% aqueous sodium hydrogen tartrate solution (approx. 150 cc). One liter amounts of ether are added three times to the reaction mixture and subsequently decanted. The organic phase is washed twice with 1 liter amounts of saturated common salt solution, dried and concentrated by evaporation in a vacuum, whereby 59 g of a mixture of the α and β isomers are obtained, and this is separated by chromatography on 9 kg of silica gel. Elution with methylene chloride/ethyl acetate (92:8) yields 30 g of the more non-polar α isomer and elution with methylene chloride/ethyl acetate (91:9) yields 9 g of the β isomer.

(c)

3α,5α-dihydroxy-2β(3'β-hydroxy-4',4'-dimethyl-trans-1-octenyl)-1α-cyclopentane-acetic acid-γ-lactone 7.3 g of β-alcohol (Example 1b) are dissolved in 306 cc of absolute methanol, and 306 g of sodium in 15.3 cc of absolute methanol are added under nitrogen and the mixture is allowed to stand at room temperature for 5 hours. The reaction mixture is subsequently cooled with an ice bath, and 26 cc of a 10% solution of tartaric acid in methanol are added within 20 minutes. After removing the solvent by distillation in a vacuum, the crystalline residue is distributed between methylene chloride and a saturated common salt solution, the organic phase is dried and concentrated by evaporation, the crystalline residue is chromatographed on 500 g of silica gel with benzene +5% of acetone, whereby 5.0 g of the diol are obtained as viscous oil.

Thin layer chromatogram toluene:acetone 2:1 RF=0.2.

(d)

3α,5α-dihydroxy-2β(3'β-hydroxy-4',4'-dimethyl-trans-1-octenyl)-1α-cyclopentane-acetic acid-γ-lactone-3,3'-bis-tetrahydropyranyl ether A solution of 5 g of the diol (Example 1c) in 285 cc of absolute toluene is added at −10° to a solution of 4.28 g of dihydropyran, 100 mg of p-toluenesulphonic acid in 40.7 cc of absolute toluene and the mixture is stirred at room temperature for 1½ hours. Washing is then effected with 150 cc of a 10% potassium bicarbonate solution and subsequently with 400 cc of a saturated common salt solution. The aqueous phases are again extracted with benzene, the organic phases are concentrated in a vacuum. 8.4 g of an oily crude product are obtained and are chromatographed on 450 g of silica gel. Elution with toluene=5% of acetone yields 7.0 g of the pure title compound.

(e)

2β(4',4'-dimethyl-3'β-tetrahydropyranyloxy-1'-trans-octenyl)-5α-hydroxy-3α-tetrahydropyranyloxy-cyclopentane-acetaldehyde-γ-lactol A solution of 7.0 g of the bis-tetrahydropyran ether (Example 1d) in 300 cc of absolute toluene is cooled to −70°, and 25 cc of diisobutyl-aluminium hydride solution (20% in toluene) are added within 25 minutes. After one hour, 185 cc of tetrahydrofuran/water (2:1) are added to the solution, filtration is effected, the filtrate is washed with a saturated sodium chloride solution, dried and concentrated, whereby 5.9 g of the title compound (mixture of isomers) are obtained.

(f)

16,16-dimethyl-9α-hydroxy-11α,15β-bis-tetrahydropyranyloxy-2,3-(+)-methano-prosta-5cis,13trans-dienic acid 800 mg of sodium hydride are suspended in 8.3 cc of absolute dimethyl sulphoxide and kept at 75° for 45 minutes under nitrogen. 2.8 cc of this solution are slowly added dropwise at room temperature to a prepared solution of 2.55 g of the triphenylphosphonium salt of (+)-trans-cyclopropane-1-(2-bromoethyl)carboxylic acid in 6 cc of absolute dimethyl sulphoxide, and stirring is effected under nitrogen for 80 minutes.

2.8 cc of the ylide solution described above are slowly added dropwise to a solution of 644 g of 2β-(4',4'-dimethyl-3'β-tetrahydro-pyranyloxy-1'-trans-octenyl)-5α-hydroxy-3α-tetrahydro-pyranyloxy-cyclopentane-acetaldehyde-γ-lactol in 2 cc of absolute dimethyl sulphoxide and 1 cc of absolute tetrahydrofuran. After 40 minutes at 55°, a further 2.7 cc of the ylide solution are added dropwise and stirring is continued at 55° for 2 hours. The cooled reaction mixture is poured on 120 g of ice, the pH of the aqueous phase is adjusted to 3–b 4 and this aqueous phase is then extracted 4 times with 120 cc amounts of methylene chloride. The organic phase is washed twice with water, is dried with sodium sulphate and concentrated by evaporation at reduced pressure. The resulting crude product is chromatographed on 75 g of silica gel, whereby the pure title compound is obtained with chloroform+2–3% of methanol.

Thin layer chromatography: ethyl acetate 10% methanol Rf=0.49.

IR (methylene chloride) inter alia bands at: 3500, 1710-1695, 1200, 1030 cm⁻¹.

NMR (CDCl₃) 100 megacycles per second inter alia signals

| 4 H | 5.8–5.2 ppm | vinyl protons |
|---|---|---|
| 2 H | 4.7–4.4 ppm | THP—H |
| 9 H | 0.9–0.8 ppm | methyl-H |

EXAMPLE 2

16,16-dimethyl-11α,15β-dihydroxy-9keto-2,3-(+)-methano-prosta-5cis,13trans-dienic acid 295 mg of 16,16-dimethyl-9α-hydroxy-11α,15β-bis-tetrahydro-pyranyloxy-2,3-(+)-methano-prosta-5cis,13trans-dienic acid are dissolved in 3 cc of absolute toluene, and 89 mg of tert.butyldimethylchlorosilane are added under nitrogen. The reaction solution is cooled to 0°, and a solution of 60 cc of triethylamine in 0.6 cc of absolute toluene is slowly added dropwise. After 48 hours at room temperature, the mixture is cooled to −25°, and a precooled solution of 324 mg of N-chlorosuccinimide in 13 cc of absolute toluene and 180 mg of dimethyl sulphide is slowly added dropwise within 30 minutes. After a further 2½ hours, 502 mg of triethylamine in 2 cc of pentane are added dropwise, stirring is effected at room temperature for a further 20 minutes, and working up is effected with ether/water. The residue is dissolved in 15 cc of acetic acid, tetrahydrofuran, water (3:1:1) and allowed to stand at room temperature for 43 hours. After concentrating by evaporation at reduced pressure, the residue is chromatographed on 15 g of silica gel. The pure title compound is eluted with chloroform +3% of methanol.

Thin layer chromatography: chloroform 10% methanol RF=0.27.

IR (methylene chloride) inter alia bands at: 3600, 1740, 1695 cm⁻¹.

NMR (CDCl₃) inter alia signals at:

| 4 H | 5.8–5.3 ppm | vinyl H |
|---|---|---|
| 4 H | 3.7–4.2 ppm | 2 × CH—OH |

EXAMPLE 3

16,16-dimethyl-15β-hydroxy-9-oxo-2,3-(+)-methano-prosta-5cis,10,13trans-trienic acid 92 mg of 16,16-dimethyl-11α,15β-dihydroxy-9-keto-2,3-(+)-methano-prosta-5cis,13trans-dienic acid are dissolved in 4 cc of acetic acid/water (9:1), and the solution is kept at 60° for 5 hours. After the addition of toluene, concentration is effected by evaporation at reduced pressure. The pure title compound is isolated by chromatography of the residue on 2.5 g of silica gel.

IR (methylene chloride) inter alia bands at: 3600, 1705, 1695 cm⁻¹.

NMR (CDCl₃) inter alia signals at:

| 9 H | approx. 0.7–1.1 ppm | —CH₃ |
|---|---|---|
| 4 H | approx. 5.2–5.85 ppm | vinyl H |
| 2 H | approx. 6.2–7.7 ppm | 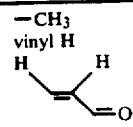 |

GROUP III

The following compounds are produced in an analogous manner to that described in Example 1 of Group II using the appropriate starting materials. The configuration of the 2,3 position is trans.

EXAMPLE 1

(5Z,9α,11α,13E,15α)-9,11,15-Trihydroxy-16-n-butyl-2,3-(−)-methano-prosta-5,13-dienic acid

EXAMPLE 2

(5Z,9α,11α,13E,15α)-9,11,15-Trihydroxy-16-n-butyl-2,3-(+)-methano-prosta-5,13-dienic acid

EXAMPLE 3

(5Z,11α,13E,15α)-11,15-Dihydroxy-16-n-butyl-9-keto-2,3-(−)-methano-prosta-5,13-dienic acid

EXAMPLE 4

(5Z,13E,15α)-15-Hydroxy-16-n-butyl-9-keto-2,3-(−)-methano-prosta-5,10,13-trienic acid

EXAMPLE 5

(5Z,11α,13E,15α)-11,15-Dihydroxy-16-n-butyl-9-keto-2,3-(+)-methano-prosta-5,13-dienic acid

EXAMPLE 6

(5Z,13E,15α)-15-Hydroxy-16-n-butyl-9-keto-2,3-(+)-methano-prosta-5,10,13-trienic acid

GROUP IV

The following compounds are produced in an analogous manner to that described in Example 1 of Group II using the appropriate starting materials. The configuration of the 2,3 position is trans.

(a) (5Z,9α,11α,13E,15α,16α)-9,11,15-Trihydroxy-16methyl- 2,3-(−)-methano-prosta-5,13-dienic acid, (b) (5Z,9α,11α,13E,15α,16β)-9,11,15-Trihydroxy-16-methyl-2,3-(−)-methano-prosta-5,13-dienic acid, (c) (5Z,11α,13E,15α,16α)-11,15-Dihydroxy-9-keto-16-methyl-2,3-(−)-methano-prosta-5,13-dienic acid, (d) (5Z,11α,13E,15α,16β)-11,15-Dihydroxy-9-keto-16-methyl-2,3-(−)-methano-prosta-5,13-dienic acid (e) (5Z,13E,15α,16α)-15-Hydroxy-9-keto-16-methyl-2,3-(−)- methano-prosta-5,10,13-trienic acid, (f) (5Z,13E,15α,16β)-15-Hydroxy-9-keto-16-methyl-2,3-(−)-methano-prosta-5,10,13-trienic acid.

In analogous manner to that described in Example 1, and additionally in the case of Examples (e) and (f) also Example 6, of Group I, the following compounds may be prepared using process (a) and/or process (b) in the case of Examples (e) and (f).

(a) (5Z,9α,11α,13E,15S,16R)-9,11,15-trihydroxy-16-methyl-2,3-trans-(−)-methylene-prosta-5,13-dienoic acid, IR (CH$_2$Cl$_2$) 3600-3400, 1695 cm$^{-1}$ b) (5Z,9α,11α,13E,15S, 16S)-9,11,15-trihydroxy-16-methyl-2,3-trans-(−)-methylene-prosta-5,13-dienoic acid, IR (CH$_2$Cl$_2$) 3600-3400, 1690-1700 cm$^{-1}$ (c) (5Z,11α,13E,15S,16R)-11,15-dihydroxy-9-keto-16-methyl-2,3-trans-(−)-methylene-prosta-5,13-dienoic acid, IR (CH$_2$Cl$_2$) 3600-3400, 1740-1695 cm$^{-1}$ (d) (5Z,11α,13E,15S,16S)-11,15-dihydroxy-9-keto-16-methyl-2,3-trans-(−)-methylene-prosta-5,13-dienoic acid, IR (CH$_2$Cl$_2$) 3600-3400, 1740-1695 cm$^{-1}$ (e) (5Z,13E,15S,16R)-15-hydroxy-9-keto-16-methyl-2,3-(−)-methylene-prosta-5,10,13-trienoic acid, IR (CH$_2$Cl$_2$) 3500, 1700 cm$^{-1}$ (f) (5Z,13E,15S,16S)-15-hydroxy-9-keto-16-methyl-2,3-(−)-methylene-prosta-5,10,13-trienoic acid, IR (CH$_2$Cl$_2$) 3600-3400, 1705-1695 cm$^{-1}$ In analogous manner the corresponding antipodes and racemates may be produced.

GROUP V

The following compounds are produced in an analogous manner to that described in Example 1 of Group II using the appropriate starting materials. The configuration of the 2,3 position is trans.

(a) (5 Z,9β,11β,13E,15S)-9,11,15-trihydroxy-2,3-(+)-trans-methylene-8,12-epi-prosta-5,13-dienoic acid, [α]$_D$ = +17.0° (c=0.9)

(b) (5Z,11β,13E,15S)-11,15-dihydroxy-2,3-(+)-trans-methylene-9-oxo-8,12-epi-prosta-5,13-dienoic acid, [α]$_D$ = +107.85° (c=0.56)

(c) (5Z,13E,15S)-15-hydroxy-2,3-(+)-trans-methylene-8,12-epi-prosta-5,10-13-trienoic acid, [α]$_D$ = −98.6° (c=1.43)

The specific rotations are given for the free acid in CHCl$_3$/CH$_3$OH 9:1.

GROUP VI

EXAMPLE I (11α,13E,15S,16R)-11,15-Dihydroxy-16-methyl-9-oxo-2,3-(−)-trans-methylene-prost-13-enoic acid (a) 400 mg of (11α,13E,15S,16R)-11,15-bis(tetrahydropyran-2-yloxy)-16-methyl-9-oxo-2,3-(−)-trans-methylene-prost-13-enoic acid is dissolved in 18 ml of a mixture of equal parts by volume of acetic acid, tetrahydrofuran and water. The reaction mixture is maintained for 36 hours at room temperature, and then evaporated under a vacuum. The residue is chromatographed on silica gel using chloroform and 2% methanol as eluant to yield the pure title compound IR 3650, 3500-3400, 1745-1740, 1700-1690 cm$^{-1}$.

The starting material may be obtained as follows:-

(b) 600 mg of sodium borohydride are suspended in 6 ml of absolute dimethyl sulphoxide and maintained at 75° for 45 minutes. After cooling of the solution, 4.5 ml thereof is added slowly dropwise to a previously prepared solution of 4.08 g of the triphenylphosphonium salt of (−)-trans-2-(2'-bromoethyl)-cycloprop-1-yl carboxylic acid in 10 ml of dimethyl sulphoxide and the resultant ylide solution is stirred for 35 minutes in a nitrogen atmosphere. 8 ml of the ylide solution is added slowly dropwise to a solution of 2.0 g of 2β-(4'R-methyl-3'S-tetrahydropyran-2-yloxy-trans-1'-octenyl)-5α-hydroxy-3α-tetrahydropyran-2-yloxy-cyclopent-1α-ylacetaldehyde γ-lactal in 6 ml of absolute tetrahydrofuran and 6 ml of dimethyl sulphoxide. After the mixture is warmed to 50° C. for 60 minutes, another 8 ml of ylide solution is added dropwise, and the mixture is maintained for a further 1 hour at 50° C. The cooled reaction mixture is poured onto 150 g of ice, and the aqueous phase adjusted to pH 3–4. The mixture is extracted three times with methylene chloride, and chromatographed on silica gel to yield on eluting with chloroform and 2% methanol, (5Z,9α,11α,13E,15S,-16R)-11,15-bis(tetrahydropyran-2-yloxy)-9-hydroxy-16-methyl-2,3-(−)-trans-methylene-prosta-5,13-dienoic acid.

IR 3600, 3550, 1730-1690 cm$^{-1}$.

(c) 1.6 g of (5Z,9α,11α,13E,15S,16R)-11,15-bis(tetrahydropyran-2-yloxy)-9-hydroxy-16-methyl-2,3-(−)-trans-methylene-prosta-5,13-dienoic acid in 150 ml of acetone is oxidized at −15° C. according to the method of Jones using the appropriate amount of a mixture of 13.34 g chromium (VI) trioxide, 10.7 ml of sulphuric acid and 35 ml of water, which mixture is added dropwise. Methanol is added after 25 minutes to the mixture, which is then stirred for 10 minutes. The mixture is poured onto 300 ml of ice-water and extracted several times with methylene chloride, to yield (5Z,11α,13E,15S,16R)-11,15-bis(tetrahydropyran-2-yloxy)-16-methyl-9-oxo-2,3-(−)-trans-methylene-prosta-5,13-dienoic acid.

IR 3500, 1740 1730, 1690 cm$^{-1}$.

(d) 460 mg of (5Z,11α,13E,15S,16R)-11,15-bis(tetrahydropyran-2-yloxy)-16-methyl-9-oxo-2,3-(−)-trans-methylene-prosta-5,13-dienoic acid in 40 ml of absolute methanol is hydrogenated for 3 hours at −15° to −10° C. in the presence of 100 mg palladium (10% w/w) on charcoal, to yield (11α,13E,15S,16R)-11,15-bis(tetrahydropyran-2-yloxy)-16-methyl-9-oxo-2,3-(−)-trans-methylene-prost-13-enoic acid.

In analogous manner to that described in Example 1, the following compounds of formula I are obtained from the corresponding 15-tetrahydropyranyl ether of formula IV, wherein $R_9$ is a group $R_3$, or when the final compound of formula I has a 11-hydroxy group, from the corresponding 11,15-bis (tetrahydropyran-2-yl) ether of formula IV, wherein $R_9$ is a group $R_3$.

EXAMPLE 2

(5Z,9α,11α,13E,15R)-15-methyl-9,11,15-trihydroxy-2,3-(−)-trans-methylene-prosta-5,13-dienoic acid methyl ester IR 3600-3400, 1710-1700 cm$^{-1}$.

EXAMPLE 3

(5Z,9α,11α,13E,15S)-15-methyl-9,11,15-trihydroxy-2,3-(−)-trans-methylene-prosta-5,13-dienoic acid methyl ester M.pt. 76°-77°.

EXAMPLE 4

(5Z,9α,11α,13E,15R)-15-methyl-9,11,15-trihydroxy-2,3-(+)-trans-methylene-prosta-5,13-dienoic acid methyl ester IR 3550, 1710 cm$^{-1}$.

EXAMPLE 5

(5Z,9α,11α,13E,15S)-15-methyl-9,11,15-trihydroxy-2,3-(+)-trans-methylene-prosta-5,13-dienoic acid methyl ester M.pt. 68°-70°.

EXAMPLE 6

(5Z,9α,11α,13E,15S)-15-methyl-9,11,15-trihydroxy-2,3-(−)-trans-methylene-prosta-5,13-dienoic acid IR 3500-3300, 1700 cm$^{-1}$.

EXAMPLE 7

(5Z,9α,11α,13E,15R)-15-methyl-9,11,15-trihydroxy-2,3-(−)-trans-methylene-prosta-5,13-dienoic acid IR 3500-3300, 1700 cm$^{-1}$.

EXAMPLE 8

(5Z,9α,11α,13E,15R)-15-methyl-9,11,15-trihydroxy-2,3-(+)-trans-methylene-prosta-5,13-dienoic acid IR 3550-3300, 1720-1680 cm$^{-1}$.

EXAMPLE 9

(5Z,9α,11α,13E,15S)-15-methyl-9,11,15-trihydroxy-2,3-(+)-trans-methylene-prosta-5,13-dienoic acid IR 3600-3300, 1720-1680 cm$^{-1}$.

EXAMPLE 10

(5Z,11α,13E,15R)-11,15-dihydroxy-15-methyl-9-oxo-2,3-(−)-trans-methylene-prosta-5,13-dienoic acid methyl ester IR 3600, 1740-1710 cm$^{-1}$.

EXAMPLE 11

(5Z,9α,13E,15R)-9,15-dihydroxy-15-methyl-11-oxo-2,3-(−)-trans-methylene-prosta-5,13-dienoic acid methyl ester IR 3600, 1740-1710 cm$^{-1}$.

EXAMPLE 12

(5Z,11α,13E,15R)-11,15-dihydroxy-15-methyl-9-oxo-2,3-(+)-trans-methylene-prosta-5,13-dienoic acid methyl ester IR 3600, 1740-1710 cm$^{-1}$.

EXAMPLE 13

(5Z,9α,13E,15R)-9,15-dihydroxy-15-methyl-11-oxo-2,3-(+)-trans-methylene-prosta-5,13-dienoic acid methyl ester IR 3600, 1740-1710 cm$^{-1}$.

EXAMPLE 14

(5Z,11α,13E,15S)-11,15-dihydroxy-15-methyl-9-oxo-2,3-(−)-trans-methylene-prosta-5,13-dienoic acid methyl ester IR 3600, 1740-1700 cm$^{-1}$.

EXAMPLE 15

(5Z,9α,13E,15S)-9,15-dihydroxy-15-methyl-11-oxo-2,3-(−)-trans-methylene-prosta-5,13-dienoic acid methyl ester IR 3600, 1740-1700 cm$^{-1}$.

EXAMPLE 16

(5Z,11α,13E,15S)-11,15-dihydroxy-15-methyl-9-oxo-2,3-(+)-trans-methylene-prosta-5,13-dienoic acid methyl ester IR 3600, 1740-1700 cm$^{-1}$.

EXAMPLE 17

(5Z,9α,13E,15S)-9,15-dihydroxy-15-methyl-11-oxo-2,3-(+)-trans-methylene-prosta-5,13-dienoic acid methyl ester IR 3600, 1740-1700 cm$^{-1}$.

EXAMPLE 18

(5Z,11α,13E,15R)-11,15-dihydroxy-15-methyl-9-oxo-2,3-(−)-trans-methylene-prosta-5,13-dienoic acid IR 3600, 3400, 1735, 1695 cm$^{-1}$.

EXAMPLE 19

(5Z,11α,13E,15R)-11,15-dihydroxy-15-methyl-9-oxo-2,3-(+)-trans-methylene-prosta-5,13-dienoic acid IR 3600, 3500-3400, 1735, 1695 cm$^{-1}$.

EXAMPLE 20

(5Z,9α,13E,15R)-9,15-dihydroxy-15-methyl-11-oxo-2,3-(−)-trans-methylene-prosta-5,13-dienoic acid.

IR 3600, 3500-3400, 1740-1730, 1700-1690 cm$^{-1}$.

EXAMPLE 21

(5Z,9α,13E,15R)-9,15-dihydroxy-15-methyl-11-oxo-2,3-(+)-trans-methylene-prosta-5,13-dienoic acid IR 3600, 3500-3400, 1740-1730, 1700-1690 cm$^{-1}$.

EXAMPLE 22

(5Z,11α,13E,15S)-11,15-dihydroxy-15-methyl-9-oxo-2,3-(−)-trans-methylene-prosta-5,13-dienoic acid IR 3600-3300, 1740-1760 cm$^{-1}$.

EXAMPLE 23

(5Z,11α,13E,15S)-11,15-dihydroxy-15-methyl-9-oxo-2,3-(+)-trans-methylene-prosta-5,13-dienoic acid IR 3550, 3450, 1735, 1690 cm$^{-1}$.

EXAMPLE 24

(5Z,9α,13E,15S)-9,15-dihydroxy-15-methyl-11-oxo-2,3-(−)-trans-methylene-prosta-5,13-dienoic acid IR 3600, 3500-3400, 1740-1730, 1695 cm$^{-1}$.

EXAMPLE 25

(5Z,9α,13E,15S)-9,15-dihydroxy-15-methyl-11-oxo-2,3-(+)-trans-methylene-prosta-5,13-dienoic acid IR 3600, 3500-3400, 1740-1730, 1700-1690 cm$^{-1}$.

EXAMPLE 26

(5Z,9α,11α,15S)-16,16-dimethyl-9,11,15-trihydroxy-2,3-(−)-trans-methylene-prost-5-enoic acid IR 3600, 3500, 1690 cm$^{-1}$.

EXAMPLE 27

(5Z,9α,11α,15S)-16,16-dimethyl-9,11,15-trihydroxy-2,3-(+)-trans-methylene-prost-5-enoic acid IR 3600, 3500-3400, 1700-1690 cm$^{-1}$.

EXAMPLE 28

(5Z,11α,15S)-11,15-dihydroxy-16,16-dimethyl-9-oxo-2,3-(−)-trans-methylene-prost-5-enoic acid IR 3600, 3450, 1735, 1690 cm$^{-1}$.

EXAMPLE 29

(5Z,11α,15S)-11,15-dihydroxy-16,16-dimethyl-9-oxo-2,3-(+)-trans-methylene-prost-5-enoic acid IR 3600, 3500-3400, 1740-1730, 1690 cm$^{-1}$.

EXAMPLE 30

(5Z,15S)-16,16-dimethyl-15-hydroxy-9-oxo-2,3-(−)-trans-methylene-prosta-5,10-dienoic acid IR 3500, 1730, 1690 cm$^{-1}$.

EXAMPLE 31

(5Z,15S)-16,16-dimethyl-15-hydroxy-9-oxo-2,3-(+)-trans-methylene-prosta-5,10-dienoic acid IR 3600, 3500, 1735-1730, 1695-1690 cm$^{-1}$.

EXAMPLE 32

(9α,11α,13E,15R)-16,16-dimethyl-9,11,15-trihydroxy-2,3-(+)-trans-methylene-prost-13-enoic acid IR 3600-3400, 1695 cm$^{-1}$.

EXAMPLE 33

(9α,11α,13E,15S)-16-n-butyl-9,11,15-trihydroxy-2,3-(−)-trans-methylene-prost-13-enoic acid IR 3600, 3500-3400, 1700-1690 cm$^{-1}$.

EXAMPLE 34

(9α,11α,13E,15S)-16-n-butyl-9,11,15-trihydroxy-2,3-(+)-trans-methylene-prost-enoic acid IR 3600, 3500-3400, 1700-1690 cm$^{-1}$.

EXAMPLE 35

(11α,13E,15R)-11,15-dihydroxy-16,16-dimethyl-9-oxo-2,3-(+)-trans-methylene-prost-13-enoic acid IR 3400, 1735, 1690 cm$^{-1}$.

EXAMPLE 36

(11α,13E,15S)-16-n-butyl-11,15-dihydroxy-9-oxo-2,3-(−)-trans-methylene-prost-13-enoic acid IR 3600, 3400, 1740-1730, 1690 cm$^{-1}$.

EXAMPLE 37

(11α,13E,15S)-16-n-butyl-11,15-dihydroxy-9-oxo-2,3-(+)-trans-methylene-prost-13-enoic acid IR 3600, 3500-3400, 1735, 1700-1690 cm$^{-1}$.

EXAMPLE 38

(13E,15R)-16,16-dimethyl-15-hydroxy-9-oxo-2,3-(+)-trans-methylene-prosta-10,13-dienoic acid IR 3600, 1695 cm$^{-1}$.

EXAMPLE 39

(13E,15S)-16-n-butyl-15-hydroxy-9-oxo-2,3-(−)-trans-methylene-prosta-10,13-dienoic acid IR 3600, 3500-3400, 1700-1690 cm$^{-1}$.

EXAMPLE 40

(13E,15S)-16-n-butyl-15-hydroxy-9-oxo-2,3-(+)-trans-methylene-prosta-10,13-dienoic acid IR 3600, 1695 cm$^{-1}$.

EXAMPLE 41

(9α,11α,15R)-16,16-dimethyl-9,11,15-trihydroxy-2,3-(+)-trans-methylene-prostanoic acid IR 3600-3400, 1695 cm$^{-1}$.

EXAMPLE 42

(9α,11α,15R)-16,16-dimethyl-9,11,15-trihydroxy-2,3-(−)-trans-methylene-prostanoic acid IR 3600, 3500-3400, 1700-1690 cm$^{-1}$.

EXAMPLE 43

(9α,11α,15R)-16-n-butyl-9,11,15-trihydroxy-2,3-(−)-trans-methylene-prostanoic acid IR 3600, 3500-3400, 1695 cm$^{-1}$.

EXAMPLE 44

(9α,11α,15R)-16-n-butyl-9,11,15-trihydroxy-2,3-(+)-trans-methylene-prostanoic acid IR 3600-3400, 1695 cm$^{-1}$.

EXAMPLE 45

(11α,15S)-11,15-dihydroxy-9-oxo-2,3-(−)-trans-methylene-prostanoic acid

IR 3600, 3400, 1735, 1690 cm$^{-1}$.

EXAMPLE 46

(11α,15S)-11,15-dihydroxy-9-oxo-2,3-(+)-trans-methylene-prostanoic acid

IR 3600, 3400, 1740-1730, 1690 cm$^{-1}$.

EXAMPLE 47

(11α,15S)-11,15-dihydroxy-16,16-dimethyl-9-oxo-2,3-(−)-trans-methylene-prostanoic acid IR 3600, 3500-3400, 1735, 1700-1690 cm$^{-1}$.

EXAMPLE 48

(11α,15R)-11,15-dihydroxy-16,16-dimethyl-9-oxo-2,3-(+)-trans-methylene-prostanoic acid IR 3600, 3500-3400, 1740-1730, 1700-1690 cm$^{-1}$.

EXAMPLE 49

(11α,15R)-16-n-butyl-11,15-dihydroxy-9-oxo-2,3-(−)-trans-methylene-prostanoic acid IR 3600, 3500-3400, 1740-1730, 1695 cm$^{-1}$.

EXAMPLE 50

(11α,15R)-16-n-butyl-11,15-dihydroxy-9-oxo-2,3-(+)-trans-methylene-prostanoic acid IR 3600, 3500-3300, 1740-1730, 1695 cm$^{-1}$.

EXAMPLE 51

(15S)-15-hydroxy-9-oxo-2,3-(−)-trans-methylene-prost-10-enoic acid

IR 3600-3400, 1730-1680 cm$^{-1}$.

EXAMPLE 52

(15S)-15-hydroxy-9-oxo-2,3-(+)-trans-methylene-prost-10-enoic acid

IR 3600, 3500-3400, 1730-1680 cm$^{-1}$.

EXAMPLE 53

(15R)-16-n-butyl-15-hydroxy-9-oxo-2,3-(−)-trans-methylene-prost-10-enoic acid

IR 3600-3400, 1730-1680 cm$^{-1}$.

EXAMPLE 54

(15R)-16-n-butyl-15-hydroxy-9-oxo-2,3-(+)-trans-methylene-prost-10-enoic acid

IR 3600-3400, 1725-1685 cm$^{-1}$.

EXAMPLE 55

(15S)-16,16-dimethyl-15-hydroxy-9-oxo-2,3-(−)-trans-methylene-prost-10-enoic acid IR 3600-3400, 1730-1680 cm$^{-1}$.

EXAMPLE 56

(15R)-16,16-dimethyl-15-hydroxy-9-oxo-2,3-(+)-trans-methylene-prost-10-enoic acid IR 3600-3400, 1725-1680 cm$^{-1}$.

EXAMPLE 57

(9α,11α,15S)-9,11,15-trihydroxy-2,3-(−)-trans-methylene-prostanoic acid

IR 3600-3400, 1710-1680 cm$^{-1}$.

EXAMPLE 58

(9α,11α,15S)-9,11,15-trihydroxy-2,3-(+)-trans-methylene-prostanoic acid

IR 3600, 3500-3400, 1700-1690 cm$^{-1}$.

EXAMPLE 59

(9α,11α,13E,15R)-16,16-dimethyl-9,11,15-trihydroxy-2,3-(−)-trans-methylene-prost-13-enoic acid IR 3600-3400, 1695 cm$^{-1}$.

EXAMPLE 60

(11α,13E,15R)-11,15-dihydroxy-16,16-dimethyl-9-oxo-2,3-(−)-trans-methylene-prost-13-enoic acid IR 3600-3400, 1735, 1690 cm$^{-1}$.

EXAMPLE 61

(13E,15R)-16,16-dimethyl-15-hydroxy-9-oxo-2,3-(−)-trans-methylene-prosta-10,13-dienoic acid IR 3600, 1695 cm$^{-1}$.

EXAMPLE 62

(9α,11α,13E,15S)-9,11,15-trihydroxy-2,3-(−)-trans-methylene-prost-13-enoic acid

IR 3600-3400, 1695 cm$^{-1}$.

EXAMPLE 63

(9α,11α,13E,15S)-9,11,15-trihydroxy-2,3-(+)-trans-methylene-prost-13-enoic acid

IR 3600, 3500-3400, 1700-1690 cm$^{-1}$.

EXAMPLE 64

(11α,13E,15S)-11,15-dihydroxy-9oxo-2,3-(−)-trans-methylene-prost-13-enoic acid

IR 3600-3400, 1735, 1690 cm$^{-1}$.

EXAMPLE 65

(11α,13E,15S)-11,15-dihydroxy-9oxo-2,3-(+)-trans-methylene-prost-13-enoic acid

IR 3600, 3500-3400, 1735, 1700-1690 cm$^{-1}$.

EXAMPLE 66

(13E,15S)-15-hydroxy-9-oxo-2,3-(−)-trans-methylene-prosta-10,13-dienoic acid

IR 3600, 1720, 1695 cm$^{-1}$.

EXAMPLE 67

(13E,15S)-15-hydroxy-9-oxo-2,3-(+)-trans-methylene-prosta-10,13-dienoic acid

IR 3600-3400, 1725-1710, 1700-1690 cm$^{-1}$.

EXAMPLE 68

(5Z,11α,13E,15R)-11,15-dihydroxy-9-oxo-16-(3'-trifluoromethylphenoxy)-17,18,19,20-tetranor-2,3-(+)-trans-methylene-prosta-5,13-dienoic acid IR 3600-3400, 1740, 1690, 1590 cm$^{-1}$.

EXAMPLE 69

(5Z,9α,11α,13E,15R)-16-(3'-trifluoromethylphenoxy)-9,11,15-trihydroxy-17,18,19,20-tetranor-2,3-(+)-trans-methylene-prosta-5,13-dienoic acid IR 3600-3300, 1690, 1590 cm$^{-1}$.

EXAMPLE 70

(5Z,9α,11α,13E,15R)-16-(3'-trifluoromethylphenoxy)-9,11,15-trihydroxy-17,18,19,20-tetranor-2,3-(−)-trans-methylene-prosta-5,13-dienoic acid IR 3600-3300, 1690, 1590 cm$^{-1}$.

EXAMPLE 71

(11α,15R)-11,15-dihydroxy-15-methyl-9-oxo-2,3-(+)-trans-methylene-prostanoic acid IR 3600, 1740-1680 cm$^{-1}$.

EXAMPLE 72

(15R)-15-hydroxy-15-methyl-9-oxo-2,3-(+)-trans-methylene-prost-10-enoic acid

IR 1740-1640 cm$^{-1}$.

EXAMPLE 73

(11α,15S)-11,15-dihydroxy-15-methyl-2,3-(+)-trans-methylene-9-oxo-prostanoic acid IR 3600-3300, 1760-1660 cm$^{-1}$.

EXAMPLE 74

(15R)-15-hydroxy-9oxo-16-(3'-trifluoromethylphenoxy)-17,18,19,20-tetranor-2,3-(+)-trans-methylene-prost-10-enoic acid methyl ester IR 3600, 1735, 1710, 1595 cm$^{-1}$.

EXAMPLE 75

(11α,13E,15R)-11,15-dihydroxy-9-oxo-16-(3'-trifluoromethylphenoxy)-17,18,19,20-tetranor-2,3-(+)-trans-methylene-prost-13-enoic acid methyl ester IR 3600-3300, 1740, 1720, 1590 cm$^{-1}$.

EXAMPLE 76

(11α,15R)-11,15-dihydroxy-9-oxo-16-(3'-trifluoromethylphenoxy)-17,18,19,20-tetranor-2,3-(+)-trans-methylene-prostanoic acid methyl eser IR 3600-3400, 1740, 1720, 1590 cm$^{-1}$.

EXAMPLE 77

(5Z,13E,15R)-15-hydroxy-9-oxo-16-(3'-trifluoromethylphenoxy)-17,18,19,20-tetranor-2,3-(+)-trans-methylene-prost-5,10,13-trienoic acid IR 3600, 1700, 1590 cm$^{-1}$.

EXAMPLE 78

(5Z,9β,11α,13E,15R)-16,16-dimethyl-16-(3'-trifluoromethylphenoxy)-9,11,15-trihydroxy-17,18,19,20-tetranor-2,3-(+)-trans-methylene-prosta-5,13-dienoic acid IR 3600-3300, 1700-1680 cm$^{-1}$.

EXAMPLE 79

(5Z,9α,11α,13E,15R)-16,16-dimethyl-16-(3'-trifluoromethylphenoxy)-9,11,15-trihydroxy-17,18,19,20-tetranor-2,3-(+)-trans-methylene-prosta-5,13-dienoic acid IR 3600, 3350, 1690 cm$^{-1}$.

EXAMPLE 80

(5Z,9α,11α,13E,15R)-16,16-dimethyl-16-(3'-trifluoromethylphenoxy)-9,11,15-trihydroxy-17,18,19,20-tetranor-2,3-(−)-trans-methylene-prosta-5,13-dienoic acid IR 3500-3300, 1700-1680 cm$^{-1}$.

EXAMPLE 81

(9α,11α,13E,15S,16R)-16-methyl-9,11,15-trihydroxy-2,3-(−)-trans-methylene-prost-13-enoic acid IR 3400, 1720-1695 cm$^{-1}$.

EXAMPLE 82

(11α,15R,16R)-11,15-dihydroxy-16-methyl-9-oxo-2,3-(−)-trans-methylene-prostanoic acid IR 3600-3300, 1740-1690 cm$^{-1}$.

EXAMPLE 83

(15R,16R)-15-hydroxy-16-methyl-9-oxo-2,3-(−)-trans-methylene-prost-10-enoic acid IR 3600, 3500-3400, 1710-1695 cm$^{-1}$.

EXAMPLE 84

(13E,15S,16R)-15-hydroxy-16-methyl-9-oxo-2,3-(−)-trans-methylene-prosta-10,13-dienoic acid IR 3600, 3500, 1730-1695 cm$^{-1}$.

EXAMPLE 85

(5Z,11α,15R,16R)-11,15-dihydroxy-16-methyl-9-oxo-2,3-(−)-trans-methylene-prost-5-enoic acid IR 3600-3350, 1735-1685 cm$^{-1}$.

EXAMPLE 86

(5Z,11α,15R,16R)-11,15-dihydroxy-16-methyl-9-oxo-2,3-(−)-trans-methylene-prost-5-enoic acid methyl ester IR 3600-3450, 1750-1700 cm$^{-1}$.

EXAMPLE 87

(5Z,13E,15R)-16,16-dimethyl-15-hydroxy-9-oxo-16-(3'-trifluoromethylphenoxy)-17,18,19,20-tetranor-2,3-(+)-trans-methylene-prosta-5,10,13-trienoic acid IR 3600-3500, 1720-1680 cm$^{-1}$.

EXAMPLE 88

(5Z,11α,13E,15R)-11,15-dihydroxy-16,16-dimethyl-9-oxo-16-(3'-trifluoromethylphenoxy)-17,18,19,20-tetranor-2,3-(+)-trans-methylene-prosta-5,13-dienoic acid IR 3700-3500, 1760-1720, 1720-1680 cm$^{-1}$.

EXAMPLE 89

(5Z,15R,16R)-15-hydroxy-16-methyl-9-oxo-2,3-(−)-trans-methylene-prosta-5,10-dienoic acid IR 3600-3400, 1740-1670 cm$^{-1}$.

EXAMPLE 90

(5Z,9α,11α,13E,15R)-16,16-dimethyl-9,11,15-trihydroxy-2,3-(+)-trans-methylene-prosta-5,13-dienoic acid diphenylmethyl ester IR 3600, 3400, 1720-1715 cm$^{-1}$.

EXAMPLE 91

(11α,13E,15S,16R)-11,15-dihydroxy-16-methyl-9-oxo-2,3-(−)-trans-methylene-prost-13-enoic acid decanyl ester IR 3600, 1745, 1725, 1695 cm$^{-1}$.

EXAMPLE 92

(11β,13E,15S)-11,15-dihydroxy-9-oxo-2,3-(+)-trans-methylene-8,12-epi-prost-13-enoic acid IR 3600, 3500-2600, 1740, 1695 cm$^{-1}$.

EXAMPLE 93

(13E,15S)-15-hydroxy-9-oxo-2,3-(+)-trans-methylene-8,12-epi-prost-10,13-dienoic acid IR 3600, 3500-2600, 1700 cm$^{-1}$.

EXAMPLE 94

(15S)-15-hydroxy-9-oxo-2,3-(+)-trans-methylene-8,12-epi-prostanoic acid

IR 3600, 3500-2600, 1735 cm$^{-1}$.

EXAMPLE 95 d,l-(5Z,9α,11α,13E,15R)-16-(3'-trifluoromethylphenoxy)-9,11,15-trihydroxy-17,18,19,20-tetranor-2,3-(+)-trans-methylene-prosta-5,13-dienoic acid IR 3600-3300, 1690, 1590 cm$^{-1}$.

The 2,3-methylene prostaglandins are useful because they exhibit pharmacological activity in animals, e.g. known prostaglandin-like activity of analogous straight chain prostaglandins. In particular, the prostaglandins, especially the PGE, PGF$_α$ and PGA compounds of formula I, are useful as broncho-dilator agents, e.g. for the treatment of asthma, and agents for lowering arterial blood pressure (especially the PGA and PGE compounds of formula I) as indicated in standard prostaglandin tests, for example by their effect on the smooth muscles of the rat stomach and colon on administration of 1 to 100 mg of the compounds, in accordance with the principles of N. Gilmore et al, Nature, 218, 1135–40 (1968) and by their effect on the histamine induced bronchospasm in the guinea pig on administration of from 1 to 32 µg/kg i.v. of the compounds in accordance with the principles of Konzett H. and Roessler R., Naunyn-Schmiedberg's Archiv für experimentelle Pathologie und Pharmakologie, 195, 71, (1940).

The prostaglandins, especially the PGE and PGF$_2$-type compounds, are furthermore useful as uterus-stimulating agents as indicated in standard prostaglandin tests, for example, in the rat uterus in situ on administration of 0.1, e.g. 0.5 to 60 µg/kg animal body weight of the compounds according to the principles of Bisset G. W. et al in Memoirs of the Society for Endocrinology No. 14—Endogeneous substances affecting the myometrium (Edited by V. R. Pickles and R. J. Fitzpatrick, Cambridge University Press, 1966, p. 185–188) and in the rat uterus in vitro on administration of from 1 to 100 mg/ml of the compounds in accordance with the principles of P. Holton, Brit. J. Pharmacol., 3, 328 (1949).

Furthermore, the prostaglandins are useful as nasal decongestant agents as indicated in standard prostaglandin tests for indicating nasal decongestion in animals. They can be administered in amounts from about 10 µg/ml to about 0.1 mg/ml with a liquid pharmaceutical diluent.

Furthermore, the prostaglandins and especially the PGE$_2$ and PGF$_{2α}$ compounds of formula I are useful as inhibitors of blood platelet aggregation, as indicated in standard tests, for example, in accordance with the principles of Born, G. V. R., and Cross M. J., J. Physiol. 168, 178 (1963).

The PGE and PGF prostaglandins are, especially the PGE and PGF$_2$ compounds, furthermore useful as gastric secretion inhibitors as indicated in standard tests, for example, in rats on administration of from 1 to 100 µg/kg animal body weight of the compounds by an inhibition of penta-gastrin and histamine induced gastric secretion according to the principles of M. N. Gosh et al., Brit. J. Pharmacol., 13, 54 (1958) and F. Halter et al. in Helv. med. Acta, suppl., 50, 113 (1971).

For all the above uses, i.e. as bronchodilator agents, blood-pressure lowering agents, uterus-stimulating agents, gastric secretion inhibitor agents, nasal decongestant agents and blood platelet aggregation inhibitor agents, the dosage will, of course, vary depending on the compound employed, mode of administration and treatment desired. However, in general, satisfactory results are obtained when administered at a daily dosage of from about 0.1 µg to about 500 µg per kg animal body weight, conveniently given in divided doses 2 to 4 times a day or in sustained release form. For the larger mammals, the total daily dosage is in the range from about 0.1 to about 20 mg, and dosage forms suitable for oral administration comprise from about 0.02 mg to about 10 mg of the compounds admixed with a solid or liquid pharmaceutical carrier or diluent.

When the compounds are administered in liquid form, for example as nasal decongestant agents, they are conveniently administered in a form of a liquid pharmceutical composition containing about 10 µg to about 20 µg per ml of liquid.

Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastro-intestinal tract and thereby provide sustained action over a long period.

Compositions for inhalation therapy may be prepared in conventional manner, e.g. in the form of nebulizers, vaporizers and aerosols. Unit doses may be provided by a metered value system. Such compositions are especially useful for the bronchospasmolytic use of the compounds. Propellants that may be used in such compositions include fluorinated hydrocarbons.

The acidic compounds of formula I may be administered in pharmaceutically acceptable salt form. Such salt forms exhibit the same order of activity as the free acid forms. Representative salt forms include alkali metal salts such as the sodium or potassium salt, alkaline earth metal salts such as the calcium salt and also include organic salts such as the ammonium salt and amine salts such as the dimethylamine, diethylamine, trimethylamine and benzylamine salts.

I claim:

1. A compound of the formula

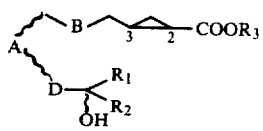

where $R_1$ is a radical of formula III,

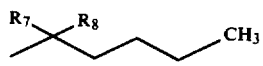

wherein $R_7$ and $R_8$ are, independently, hydrogen or alkyl of 1 to 4 carbon atoms, and $R_2$ is hydrogen, and A is a group of the formula

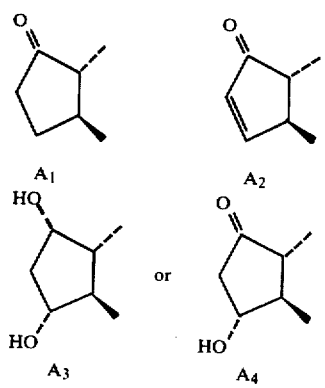

and

B is (cis—CH=CH— and
D is (trans)—CH=CH— and
$R_3$ is
(i) hydrogen
(ii) alkyl of 1 to 8 carbon atoms,
(iii) cycloalkyl of 3 to 10 carbon atoms, or
(iv) aralkyl of 7 to 12 carbon atoms.

2. A compound of claim 1, wherein $R_3$ is hydrogen, alkyl of 1 to 8 carbon atoms, or aralkyl of 7 to 12 carbon atoms.

3. A compound of claim 1, wherein A is A1.
4. A compound of claim 1, wherein A is A2.
5. A compound of claim 1, wherein A is A3.
6. A compound of claim 1, wherein A is A4.
7. A compound of claim 1, wherein the 15-hydroxy group is in the α-configuration.
8. A compound of claim 7, wherein, in the radical of formula III, $R_7$ and $R_8$ are identical.
9. A compound of claim 1 in racemic form.
10. A compound of claim 1 in individual optical form substantially free from its optical antipode.
11. A compound of claim 1, in individual optical isomer form having the same absolute configuration at C2 and C3 as 16,16-dimethyl-2,3-trans(+)-methano-prostaglandin $F_{2\alpha}$ of $[\alpha]_D^{20}=+88°$ (c=1.01, CHCl$_3$).
12. A compound of claim 1 in individual optical isomer form having the opposite absolute configuration at C2 and C3 as 16,16-dimethyl-2,3-trans(+)-methano-prostaglandin-$F_{2\alpha}$ of $[\alpha]_D^{20}=+88°$ (C=1.01, CHCl$_3$).
13. A compound of claim 1, in which the configuration of the C-15 hydroxyl group is the same as that at C-15 in 16,16-dimethyl-2,3-trans(+)-methano-prostaglandin $F_{2\alpha}$ of $[\alpha]_D^{20}=+88°$ (c=1.01, CHCl$_3$).
14. A compound of claim 1, in which the configuration of the C-15 hydroxyl group is opposite to that at C-15 in 16,16-dimethyl-2,3-trans(+)-methano-prostaglandin $F_{2\alpha}$ having $[\alpha]_D^{20}=+88°$ (c=1.01, CHCl$_3$).
15. A pharmaceutical composition for use in stimulating the uterus, inhibiting gastric secretions, inhibiting blood platelet-aggregation and decongesting the nasal passage comprising an effective amount of a compound of claim 1 in association with a pharmaceutical carrier or diluent.
16. The compound of claim 1 which is 16,16-dimethyl-2,3-trans(−)-methano-prostaglandin $E_2$.
17. The compound of claim 1 which is 2,3-trans-methano-prostaglandin $F_{2\alpha}$.
18. The compound of claim 1 which is 16,16-dimethyl-2,3-trans(+)-methano-prostaglandin $F_{2\alpha}$.
19. The compound of claim 1 which is 16,16-dimethyl-2,3-trans(−)-methano-prostaglandin $E_2$.
20. The compound of claim 1 which is 16,16-dimethyl-2,3-trans(−)-methano-prostaglandin $F_{2\alpha}$.
21. The compound of claim 1 which is 16,16-dimethyl-2,3-trans(+)-methano-prostaglandin $A_2$.
22. The compound of claim 1 which is 16,16-dimethyl-2,3-trans(−)-methano-prostaglandin $A_2$.
23. The compound of claim 1 which is 16,16-dimethyl-9α-11α-15β-trihydroxy-2,3-(+)-methano-prosta-5-cis, 13-trans-dienic acid.
24. The compound of claim 1 which is 16,16-dimethyl-11α,15β-dihydroxy-9-keto-2,3-(+)-methano-prosta-5-cis, 13-trans-dienic acid.
25. The compound of claim 1 which is 16,16-dimethyl-15β-hydroxy-9-oxo-2,3-(+)-methano-prosta-5-cis, 10,13-trans-trienic acid.
26. A compound of the formula

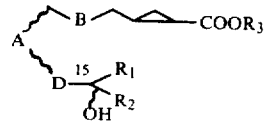

wherein

A is a group of the formula

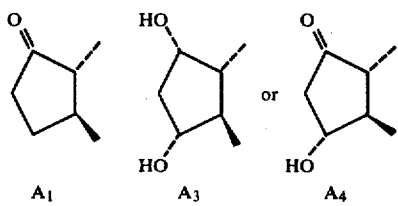

B is (cis)-CH=CH-, and

D is (trans)-CH=CH-, and $R_1$ is n-pentyl, and $R_2$ is alkyl of 1 to 7 carbon atoms, and $R_3$ is (i) hydrogen, (ii) alkyl of 1 to 8 carbon atoms (iii) cycloalkyl of 3 to 10 carbon atoms or (iv) aralkyl of 7 to 12 carbon atoms.

27. The compound of claim 1 which is (5Z,9α,11α, 13E,15R)-15-methyl-9,11,15-trihydroxy-2,3-(—)-trans-methylene-prosta-5,13-dienoic acid methyl ester.

28. The compound of claim 1 which is (5Z,9α,11α, 13E,15S)-15-methyl-9,11,15-trihydroxy-2,3-(—)-trans-methylene-prosta-5,13-dienoic acid methyl ester.

29. The compound of claim 1 which is (5Z,9α,11α, 13E,15R)-15-methyl-9,11,15-trihydroxy-2,3-(+)-trans-methylene-prosta-5,13-dienoic acid methyl ester.

30. The The compound of claim 1 which is (5Z,9α,11α, 13E,15S)-15-methyl-9,11,15-trihydroxy-2,3-(+)-trans-methylene-prosta-5,13-dienoic acid methyl ester.

31. The compound of claim 1 which is (5Z,9α,11α, 13E,15S)-15-methyl-9,11,15-trihydroxy-2,3-(—)-trans-methylene-prosta-5,13-dienoic acid.

32. The compound of claim 1 which is (5Z,9α,11α, 13E,15R)-15-methyl-9,11,15-trihydroxy-2,3-(—)-trans-methylene-prosta-5,13-dienoic acid.

33. The compound of claim 1 which is (5Z,9α,11α, 13E,15R)-15-methyl-9,11,15-trihydroxy-2,3-(+)-trans-methylene-prosta-5,13-dienoic acid.

34. The compound of claim 1 which is (5Z,9α,11α, 13E,15S)-15-methyl-9,11,15-trihydroxy-2,3-(+)-trans-methylene-prosta-5,13-dienoic acid.

35. The compound of claim 1 which is (5Z,11α,13E, 15S)-11,15-dihydroxy-15-methyl-9-oxo-2,3-(—)-trans-methylene-prosta-5,13-dienoic acid methyl ester.

36. The compound of claim 1 which is (5Z,11α,13E, 15S)-11,15-dihydroxy-15-methyl-9-oxo-2,3-(+)-trans-methylene-prosta-5,13-dienoic acid methyl ester.

37. The compound of claim 1 which is (5Z,11α,13E, 15R)-11,15-dihydroxy-15-methyl-9-oxo-2,3-(—)-trans-methylene-prosta-5,13-dienoic acid.

38. The compound of claim 1 which is (5Z, 11α, 13E, 15R)-11,15-dihydroxy-15-methyl-9-oxo-2,3-(+)-trans-methylene-prosta-5,13-dienoic acid.

39. The The compound of claim 1 which is (5Z, 11α, 13E, 15S)-11,15-dihydroxy-15-methyl-9-oxo-2,3-(—)-trans-methylene-prosta-5,13-dienoic acid.

40. The compound of claim 1 which is (5Z, 11α, 13E, 15S)-11,15-dihydroxy -15-methyl-9-oxo-2,3-(+)-trans-methylene-prosta-5,13-dienoic acid.

41. A compound selected from the group consisting of (a) (5Z, 9α, 13E, 15S)- 9, 15-dihydroxy-15-methyl-11-oxo-2,3-(—)-trans-methylene-prosta-5,13-dienoic acid methyl ester; (b) (5Z, 9α, 13E, 15S)-9,15-dihydroxy-15-methyl-11-oxo-2,3-(+)-trans-methylene-prosta-5,13-dienoic acid methyl ester: (c) (5Z, 9α, 13E, 15R)-9, 15-dihydroxy-15-methyl-11-oxo-2,3-(—)-trans-methylene-prosta-5,13-dienoic acid; (d) (5Z, 9α, 13E, 15R)-9,15-dihydroxy-15-methyl-11-oxo-2,3-(+)-trans-methylene-prosta-5,13-dienoic acid; (e) (5Z, 9α, 13E, 15S)-9,15-dihydroxy-15-methyl-11-oxo-2,3-(—)-trans-methylene-prosta-5,13-dienoic acid; (f) (5Z, 9α, 13E, 15S)-9,15-dihydroxy-15-methyl-11-oxo-2,3-(+)-trans-methylene-prosta-5,13-dienoic acid.

* * * * *